US006348450B1

(12) United States Patent
Tang et al.

(10) Patent No.: US 6,348,450 B1
(45) Date of Patent: Feb. 19, 2002

(54) NONINVASIVE GENETIC IMMUNIZATION, EXPRESSION PRODUCTS THEREFROM AND USES THEREOF

(75) Inventors: De-chu C. Tang, Birmingham, AL (US); Donald H. Marks, Rockaway, NJ (US); David T. Curiel; Zhongkai Shi, both of Birmingham, AL (US); Kent Rigby van Kampen, Hoover, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/563,826

(22) Filed: May 3, 2000

Related U.S. Application Data

(63) Continuation-in-part of application No. 09/533,149, filed on Mar. 23, 2000, which is a continuation-in-part of application No. 09/402,527, which is a continuation-in-part of application No. PCT/US98/16739, filed on Aug. 13, 1998.
(60) Provisional application No. 60/132,216, filed on May 3, 1999, provisional application No. 60/075,113, filed on Feb. 11, 1998, and provisional application No. 60/055,520, filed on Aug. 13, 1997.

(51) Int. Cl.$^7$ .......................... A61K 48/00; C12N 15/63

(52) U.S. Cl. .................. 514/44; 424/93.21; 435/320.1; 435/375

(58) Field of Search .................. 514/44; 424/93.21; 435/320.1, 375

(56) References Cited

U.S. PATENT DOCUMENTS

| | | |
|---|---|---|
| 3,608,030 A | 9/1971 | Tint |
| 3,837,340 A | 9/1974 | Counter |
| 3,906,092 A | 9/1975 | Hilleman et al. |
| 3,950,512 A | 4/1976 | Emery et al. |
| 3,962,424 A | 6/1976 | Zygraich et al. |
| 4,089,801 A | 5/1978 | Schneider |
| 4,217,344 A | 8/1980 | Vanlerberghe et al. |
| 4,235,871 A | 11/1980 | Papahadjopoulos et al. |
| 4,241,046 A | 12/1980 | Papahadjopoulos et al. |
| 4,394,448 A | 7/1983 | Szoka, Jr. et al. |

(List continued on next page.)

FOREIGN PATENT DOCUMENTS

| | | |
|---|---|---|
| EP | 286798 A2 | 10/1988 |
| EP | 298142 A1 | 1/1989 |
| EP | 406778 A1 | 1/1991 |
| EP | 0 638 316 A1 | 2/1995 |
| EP | 0 773 295 A2 | 5/1997 |
| WO | WO 90/11092 | 10/1990 |
| WO | WO 92/11028 | 7/1992 |
| WO | WO 95/05853 | 3/1995 |
| WO | WO 98/03641 | 1/1998 |
| WO | WO 99/08713 | 2/1999 |
| WO | WO 99/15683 | 4/1999 |
| WO | WO 00/66179 | 11/2000 |

OTHER PUBLICATIONS

Alexander et al, "Liposome–mediated Gene Transfer and Expression via the Skin", Human Molecular Genetics, 1995, vol. 4, No. 12, pp. 2279–2285.
Autumn et al., (2000) Nature, 405 (6787), abstract only.
Brandsman et al., (1991) PNAS USA 88:4816–4820.
Brown et al., (1997) "Adenoviral Vectors Given Intravenously to Immunocompromised Mice Yield Stable Transduction of the Colonic Epithelium", Gastroenterology, vol. 112, 1586–1594.
Carson, (1987) "Infectious diseases in day–care centers: transmission and approaches to prevention", Drug Intell. Clin. Pharm., vol. 21, No. 9, 694–701, (Abstract).
Chen et al., (1984) "Anti–hypervariable region antibody induced by a defined peptide: an approach for studying the structural corrrelates of idiotypes", Proc. Natl. Acad. Sci. USA, vol. 81, No. 6, 1784–1788, (Abstract).
Chen et al., (1984) "Delineation of a cross–reactive idiotype on human autoantibodies with antibody against a synthetic peptide", J. Exp. Med., vol. 159, No. 5, 1502–1511, (Abstract).
Chen et al., (1985) "Characterization of an epibody. An antiidiotype that reacts with both the idiotype of rheumatoid factors (RF) and the antigen recognized by RF.", J. Exp. Med., vol. 161, No. 2, 323–331, (Abstract).

(List continued on next page.)

Primary Examiner—Deborah Crouch
Assistant Examiner—Joseph T. Woitach
(74) Attorney, Agent, or Firm—Frommer Lawrence & Haug LLP; William S. Frommer; Thomas J. Kowalski

(57) ABSTRACT

Disclosed and claimed are methods of non-invasive genetic immunization in an animal and/or methods of inducing a systemic immune or therapeutic response in an animal, products therefrom and uses for the methods and products therefrom. The methods can include contacting skin of the animal with a vector in an amount effective to induce the systemic immune or therapeutic response in the animal. The vector can include and express an exogenous nucleic acid molecule encoding an epitope or gene product of interest. The systemic immune response can be to or from the epitope or gene product. The nucleic acid molecule can encode an epitope of interest and/or an antigen of interest and/or a nucleic acid molecule that stimulates and/or modulates an immunological response and/or stimulates and/or modulates expression, e.g., transcription and/or translation, such as transcription and/or translation of an endogenous and/or exogenous nucleic acid molecule; e.g., one or more of influenza hemagglutinin, influenza nuclear protein, tetanus toxin C-fragment, anthrax protective antigen, HIV gp 120, human carcinoembryonic antigen, and/or a therapeutic, an immunomodulatory gene, such as co-stimulatory gene and/or or a cytokine gene. The immune response can be induced by the vector expressing the nucleic acid molecule in the animal's cells. The immune response can be against a pathogen or a neoplasm. A prophylactic vaccine or a therapeutic vaccine or an immunological composition can include the vector.

52 Claims, 19 Drawing Sheets

U.S. PATENT DOCUMENTS

| | | | |
|---|---|---|---|
| 4,405,616 A | 9/1983 | Rajadhyaksha | |
| 4,557,934 A | 12/1985 | Cooper | |
| 4,594,244 A | 6/1986 | Lehner et al. | |
| 4,623,541 A | 11/1986 | Elliot et al. | |
| 4,674,490 A | 6/1987 | Frankel et al. | |
| 4,738,846 A | 4/1988 | Rose et al. | |
| 4,775,630 A | 10/1988 | Tibbetts et al. | |
| 4,797,368 A | 1/1989 | Carter et al. | |
| 4,806,350 A | 2/1989 | Gerber | |
| 4,863,970 A | 9/1989 | Patel et al. | |
| 4,929,442 A | 5/1990 | Powell | |
| 4,944,942 A | 7/1990 | Brown et al. | |
| 5,023,252 A | 6/1991 | Hseih | |
| 5,139,941 A | 8/1992 | Muzyczka et al. | |
| 5,206,163 A | 4/1993 | Renard et al. | |
| 5,494,807 A | 2/1996 | Paoletti et al. | |
| 5,505,945 A | 4/1996 | Gristina et al. | |
| 5,530,102 A | 6/1996 | Gristina et al. | |
| 5,547,932 A | 8/1996 | Curiel et al. | |
| 5,552,309 A | 9/1996 | March | |
| 5,580,859 A | 12/1996 | Felgner et al. | |
| 5,585,362 A | 12/1996 | Wilson et al. | |
| 5,589,466 A | 12/1996 | Felgner et al. | |
| 5,591,439 A | 1/1997 | Plotkin et al. | |
| 5,593,972 A | 1/1997 | Weiner et al. | |
| 5,616,329 A | 4/1997 | Newman et al. | |
| 5,635,380 A | 6/1997 | Naftilan et al. | |
| 5,645,834 A | 7/1997 | Cockrum | |
| 5,648,096 A | 7/1997 | Gander et al. | |
| 5,658,785 A | 8/1997 | Johnson | |
| 5,662,098 A | 9/1997 | Yoshida | |
| 5,665,362 A | 9/1997 | Inglis et al. | |
| 5,670,488 A | 9/1997 | Gregory et al. | |
| 5,679,647 A | 10/1997 | Carson et al. | |
| 5,693,622 A | 12/1997 | Wolff et al. | |
| 5,698,202 A | 12/1997 | Ertl et al. | |
| 5,698,443 A | 12/1997 | Henderson et al. | |
| 5,700,470 A | 12/1997 | Saito et al. | |
| 5,700,680 A | 12/1997 | Newton et al. | |
| 5,700,910 A | 12/1997 | Metzger et al. | |
| 5,703,055 A | 12/1997 | Felgner et al. | |
| 5,705,151 A | 1/1998 | Dow et al. | |
| 5,707,618 A | 1/1998 | Armentano et al. | |
| 5,707,812 A | 1/1998 | Horn et al. | |
| 5,716,613 A | 2/1998 | Guber et al. | |
| 5,718,902 A | 2/1998 | Yilma et al. | |
| 5,731,172 A | 3/1998 | Saito et al. | |
| 5,731,181 A | 3/1998 | Kmiec | |
| 5,736,387 A | 4/1998 | Paul et al. | |
| 5,739,118 A | * 4/1998 | Carrano et al. | |
| 5,753,263 A | * 5/1998 | Lishko et al. | |
| 5,753,500 A | * 5/1998 | Shenk et al. | |
| 5,756,086 A | * 5/1998 | McClelland et al. | |
| 5,762,939 A | * 6/1998 | Smith et al. | |
| 5,763,270 A | * 6/1998 | Eastman et al. | |
| 5,766,599 A | * 6/1998 | Paoletti et al. | |
| 5,770,442 A | * 6/1998 | Wickham et al. | |
| 5,780,280 A | * 7/1998 | Lebkowski et al. | |
| 5,780,448 A | * 7/1998 | Davis | |
| 5,786,211 A | * 7/1998 | Johnson | |
| 5,789,390 A | * 8/1998 | Descamps et al. | |
| 5,792,462 A | * 8/1998 | Johnston et al. | |
| 5,795,972 A | * 8/1998 | Kmiec | |
| 5,804,566 A | * 9/1998 | Carson et al. | |
| 5,817,492 A | * 10/1998 | Saito et al. | |
| 5,817,637 A | * 10/1998 | Weiner et al. | |
| 5,820,868 A | * 10/1998 | Mittal et al. | |
| 5,824,538 A | * 10/1998 | Brandstrom et al. | |
| 5,824,544 A | * 10/1998 | Armentano et al. | |
| 5,830,177 A | * 11/1998 | Li et al. | |
| 5,830,463 A | * 11/1998 | Duke et al. | |
| 5,830,730 A | * 11/1998 | German et al. | |
| 5,834,256 A | * 11/1998 | Finer et al. | |
| 5,846,559 A | * 12/1998 | Hopp | |
| 5,849,719 A | * 12/1998 | Carson et al. | |
| 5,851,806 A | * 12/1998 | Kovesdi et al. | |
| 5,866,383 A | * 2/1999 | Moss et al. | |
| 5,872,005 A | * 2/1999 | Wang et al. | |
| 5,872,154 A | * 2/1999 | Wilson et al. | |
| 5,874,279 A | * 2/1999 | Cochran et al. | |
| 5,880,102 A | 3/1999 | George et al. | |
| 5,882,877 A | 3/1999 | Gregory et al. | |
| 5,885,808 A | 3/1999 | Spooner et al. | |
| 5,891,690 A | 4/1999 | Massie | |
| 5,998,382 A | 12/1999 | Furth et al. | |
| 6,087,341 A | 7/2000 | Khavari | |

OTHER PUBLICATIONS

Chen et al., (1985) "Characterization of human–rheumatoid factors with seven antiidiotypes induced by synthetic hypervariable region peptides", J. Exp. Med., vol. 162, No. 2, 487–500, (Abstract).

Choate and Khavari, (1997) "Direct Cutaneous Gene Delivery in a Human Genetic Skin Disease", Human Gene Therapy 8: 1659–1665.

Ciernik et al., (1996) "Puncture–Mediated Gene Transfer to the Skin", Human Gene Therapy, vol. 7, 893–899.

Citations from BIOLOGICAL ABSTRACTS:BIO, Oct. 5, 1997.

Condon et al., (1996) "DNA–based immunization by in vitro transfection of dendritic cells", Nature Medicine, vol. 2, No. 10, 1122–1126.

Corr et al., (1996) "Gene vaccination with naked plasmid DNA: mechanism of CTL printing", J. Exp. Med. Vol. 184, No. 4, 1555–1560, (Abstract).

Corr et al., (1996) "Costimulation provided by DNA immunization enhances antitumor immunity", J. Immunol., vol. 159, No. 10, 4999–5004, (Abstract).

Donnelly et al, (1997) "DNA VACCINES", Life Sciences, vol. 60, No. 3, 163–172.

English Abstract for Canadian Patent No. 2,234,201.

English Abstract for European Patent Appln. No. 88–080256190 (US Patent 4,623,544).

English Abstract for European Patent Appln. No. 88–420286798 (EP Patent 0286798).

English Abstract for European Patent Appln. No. 89–020298142 (EP Patent 0298142).

English Abstract for European Patent Appln. No. 91–020406778 (EP Patent 0406778).

English Abstract for International Patent WO 94/10323.

English Abstract from German Patent No. DE 3937412.

Fong et al., (1986) "The common occurence of internal image type anti–idiotypic antibodies in rabbits immunized with monoclonal and polyclonal human IgM rheumatoid factors", Clin. Exp. Immunol., vol. 64, No. 3, 570–580, (Abstract).

Goldman et al., (1997) "In vitro and in vivo gene delivery mediated by a synthetic polycationic amino polymer," Nature Biotechnology, vol. 15, 462–466.

Goni et al., (1985) "Sequence similarities and cross–idiotypic specificity of L chains among human monoclonal IgM kappa with anti–gamma–globulin activity", J. Immunol., vol. 135, No. 6, 4073–4079, (Abstract).

Greenhalgh et al., (1994) "Epidermis: An Attractive Target Tissue for Gene Therapy", Gene Therapy, vol. 103, No. 5, 63S–69S.

Guo, Z. et al., J. Neurosci. Res., vol. 43, No. 1, 32–41, Jan. 1, 1996 (Abstract).

Hong et al., (1999) "Topical Gene Delivery to Murine Skin", The Society for Investigative Dermatology, Inc., 370–373.

Huyghe et al., (1995) "Purification of a Type 5 Recombinant Adenovirus Encoding Human p53 by Column Chromatography", Human Gene Therapy, vol. 6, 1403–1416.

Johnston et al., (1993) "The Use of Microparticle Injection to Introduce Genes Into Animal Cells In Vitro and In Vivo", Genetic Engineering, vol. 15, 225–234.

Khavari, P., (1997) Molecular Medicine Today, vol. 3, 533–538.

Krawczynski et al., (1996) "Effect of immune globulin on the prevention of experimental hepatitis C virus infection", J. Infect. Dis., vol. 173 4, 822–828, (Abstract).

Krul, (1996) "Advances in Gene Therapy: Clear Progress Despite Setbacks", Therapy Markets and Emerging Technologies Spectrum Publications, Issue 112, 47 pages, (Abstract).

Lee et al., (1997) "Inhibition of IgE antibody formation by plasmid DNA immunization is mediated by both CD4+ and CD8+ T Cells", Int. Arch Allergy Immunol. vol. 113, nos. 103, 227–230, (Abstract).

Lee et al., (1998) "Control of immune responses by gene immunization", Ann. Med. vol. 5, 46–0468, (Abstract).

Lee et al., (1998) "Induction of an antigen–specific, CD1–restricted cytotoxic T lymphocyte response In vivo", J. Exp. Med., vol. 187, No. 3, 433–438, (Abstract).

Li et al., (1995) Nature Medicine, vol. 1, No. 7, p;p. 705–706, Jul. 7.

Lu et al., (1996) Proc. Assoc. Amer. Phys., vol. 108, No. 2, 165–172, Mar.

Lu et al., (1997) "Topical Applications of Viral Vectors for Epidermal Gene Transfer", The Journal of Investigative Dermatology, vol. 108, No. 5, pp. 803–808 (Abstract).

Niemic et al., (1997) "DNA Perifollicular Transgenic Expression of Human Interleukin–1 Receptor Antagonis Protein following Topical Application of Novel Liposome––Plasmid DNA Formulations In Vivo", Journal of Pharmaceutical Sciences, vol. 86, No. 6, 701–708, Jun. 1997.

Panchagnula et al., (1997) Meth. Find. Exp. Clin. Pharmacol. 19(5):335–341.

Paul et al., (1995) "Transdermal immunization with large proteins by means of ultradeformable drug carriers", Eur. J. Immuno., vol. 25, 3521–3524.

Press Release, (1996) "Perkin–Elmer and Kimeragen to Develop Novel Gene Repair Molecules That Treat Genetic Diseases", Norwalk, CT and Newtown, PA.

Raz et al., (1994) "Intradermal gene immunization: The possible role of DNA uptake in the induction of cellular immunity to viruses", Proc. Natl. Acad. Sci. USA, vol. 91, 9519–9523.

Raz et al., (1996) "Preferential induction of a Th1 immune response and inhibition of specific IgE antibody formation by plasmid DNA immunization", Proc. Nat'l Acad. Sci. USA, vol. 93, No. 10, 5141–5145, (Abstract).

Remus et al. (1999) "Insertion of Foreign DNA into an Established Mammalian Genome Can Alter the Methylation of Cellular DNA Sequences", Journal of Virology, vol. 73, No. 2, 1010–1022.

Rhodes et al. (1987) "Autoantibodies in infectious mononucleosis having specificity for the gylcine–alanine repeating region of the Epstein–Barr virus nuclear antigen", J. Exp. Med., vol. 165, No. 4, 1026–1040, (Abstract).

Sarphie et al., (1997) "Bovailability following transdermal powdered delivery (TPD) of radiolabeled inulin to hairless guinea pigs", Journal of Controlled Release, vol. 47, 61–69.

Sato et al., (1996) "Immunostimulatory DNA sequences necessary for effective intradermal gene immunization", Science, vol. 273, No. 5273, 352–354, (Abstract).

Sawamura et al. (1997) "In Vivo Transfer of a Foreign Gene to Keratinocytes Using the Hemagglutinating Virus of Japan–Liposome Method", The Society for Investigative Dermatology, Inc., 195–199.

Shi et al., (1999) "DNA–based non–invasive vaccination onto the skin", Vaccine, vol. 17, 2136–2141.

Silverman et al., (1990) "Structural characterization of the second major cross–reactive idiotype group of human rheumatoid factors. Association with the VH4 gene family", Arthritis Rheum., vol. 33, No. 9, 1347–1360, (Abstract).

Stephenson, (1999) "New Method to Repair Faulty Genes Stirs Interest in Chimeraplasty Technique", JAMA, vol. 282, No. 2, 119–121.

Tang et al.,(1992) "Genetic immunization is a simple method for eliciting an immune response", Nature, vol. 356, 152–154.

Tang et al., (1994) "Butyrate–inducible and tumor–restricted gene expression by adenovirus vectors", Cancer Gene Therapy, vol. 1, No. 1, 15–20.

Tang et al., (1997) "Vaccination onto bare skin", Nature, vol. 388, 729–730.

Todryk et al., (1996) "Induction of immune responses to functional determinants of a cell structure streptocooal antigen", Immunology, vol. 87, 55–63.

Tsukui et al., (1996) "Transgenesis by adenovirus–meditated gene transfer into mouse zona–free eggs", Nature Biotechnology, vol. 14, 982–985.

Wang et al., (1993) "Correlation of a Deletion Mutant by Gene Targeting with an Adenovirus Vector", Molecular and Cellular Biology, vol. 13, No. 2, 918–927.

Watanabe et al., (1993) "Induction of antibodies to a kappa V region by gene immunization", J. Immunol., vol. 151, No. 5, 2871–2876, (Abstract).

Weiner N., (1998) "Targeted follicular delivery of macromolecules via liposomes", International Journal of Pharmaceuticals, vol. 162, 29–38.

Welch et al., (1983) "Increased frequency of rheumatoid factor precursor B lymphocytes after immunization of normal adults with tetanuz toxoid", Clin. Exp. Immunol., vol. 51, No. 2, 299–304, (Abstract).

Yang, N.S. et al., Nat. Med., vol. 1, No. 5, 481–481, May 1995 (Abstract).

Yokoyama et al., (1996) "DNA immunization: Effects of vehicle and route of administration on the induction of protective antiviral immunity", FEMS Immunology and Medical Microbiology, vol. 14, 221–230.

Zhdanov et al., (1997) "Nonviral methods of gene transfer in gene therapy", Vopr Med Khim, vol. 43, No. 1, 3–12 (Abstract).

* cited by examiner

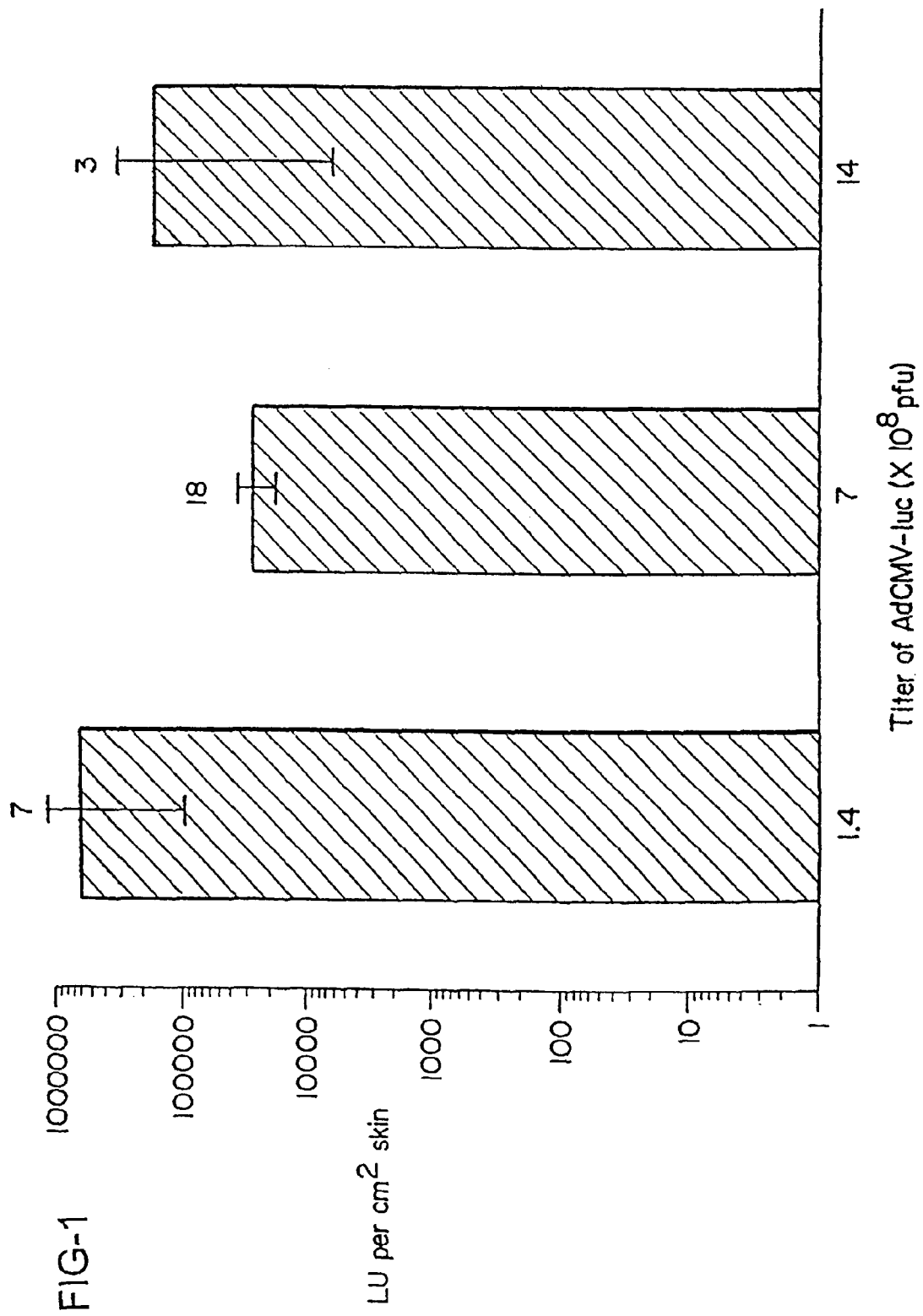

ELISA antibodies generated by the AdCMV-PR8ha vector in a pigtail mac

Relocation of luciferase spots in skin after topical application of an adenovirus vector.

ELISA antibodies generated in mice by vaccine patches with or without pre-treatment using a depilatory agent.

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 1
gcgccattct atcctctaga        20

<210> SEQ ID NO 2
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 2
acaatttgga ctttccgccc        20

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 3
gtaccagagt cctttgatcg        20

<210> SEQ ID NO 4
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 4
ccctcgggtg taatcagaat        20

<210> SEQ ID NO 5
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: primer

<400> SEQUENCE: 5
cgtctgaaga taccttcaa        19

<210> SEQ ID NO 6
<211> LENGTH: 20
<212> TYPE: DNA
<213> ORGANISM: Artificial Sequence

```
<220> FEATURE:
<221> NAME/KEY: misc_feature
<222> LOCATION: (1)..(20)
<223> OTHER INFORMATION: primer

<400> SEQUENCE: 6
accagtccca tgaaaatgac                                              20

<210> SEQ ID NO 7
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 7
ggctcctttg catgtaacag                                              20

<210> SEQ ID NO 8
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 8
cctactgtaa tggcacctgt                                              20

<210> SEQ ID NO 9
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 9
atgaaggcaa acctactggt                                              20

<210> SEQ ID NO 10
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 10
gatgcatatt ctgcactgca                                              20

<210> SEQ ID NO 11
<211> LENGTH: 20
<212> TYPE: DNA
<213> ORGANISM: Artificial Sequence
<220> FEATURE:
<221> NAME/KEY: primer
<222> LOCATION: (1)..(20)
<223> OTHER INFORMATION: primer

<400> SEQUENCE: 11
gtggggtatt catcacccgt                                              20
```

```
<210> SEQ ID NO 12
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 12
tgcatagcct gatccctgtt                                          20
```

NONINVASIVE GENETIC IMMUNIZATION, EXPRESSION PRODUCTS THEREFROM AND USES THEREOF

RELATED APPLICATIONS

This application is based upon and claims priority from U.S. Provisional Application No. 60/132,216, filed May 3, 1999. This application is also a continuation-in-part status of U.S. patent application Ser. No. 09/533,149, filed Mar. 23, 2000, which is a continuation-in-part application of U.S. patent application Ser. No. 09/402,527, filed Oct. 5, 1999. U.S. application Ser. No. 09/402,527 is a national stage, continuation-in-part, application of PCT/US98/16739, filed Aug. 13, 1998, which, in turn, claims the priority of U.S. Provisional Applications Serial Nos. 60/055,520 and 60/075,113, filed Aug. 13, 1997 and Feb. 11, 1998, respectively. Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("application cited documents"). Each of the application cited documents, and each document cited or referenced in the application cited documents, is hereby incorporated herein by reference.

GOVERNMENT SUPPORT

Research carried out in connection with this invention may have been supported in part by a grant from the National Institutes of Health, Grant No. 1-R43-AI-43802. The United States government may have certain rights in the invention.

FIELD OF THE INVENTION

The present invention relates generally to the fields of immunology and vaccine technology. The present invention also relates to techniques of skin-targeted non-invasive gene delivery to elicit immune responses and uses thereof. The invention further relates to methods of non-invasive genetic immunization in an animal and/or methods of inducing an immunulogical, e.g., systemic immune response or a therapeutic, e.g., a systemic therapeutic response, in an animal, products therefrom and uses for the methods and products therefrom. The invention yet further relates to such methods comprising contacting skin of the animal with a vector in an amount effective to induce the response, e.g., systemic immune response, in the animal. Even further, the invention relates to such methods wherein the vector comprises and express an exogenous nucleic acid molecule encoding an epitope or gene product of interest, e.g., an antigen or therapeutic. Still further, the invention relates to such methods wherein the response, e.g., systemic immune or therapeutic response, can be to or from the epitope or gene product.

The invention yet further still relates to such methods wherein the nucleic acid molecule can encode an epitope of interest and/or an antigen of interest and/or a nucleic acid molecule that stimulates and/or modulates an immunological response and/or stimulates and/or modulates expression, e.g., transcription and/or translation, such as transcription and/or translation of an endogenous and/or exogenous nucleic acid molecule. The invention additionally relates to such methods wherein the nucleic acid molecule can be exogenous to the vector. The invention also relates to such methods wherein the exogenous nucleic acid molecule encodes one or more of an antigen or portion thereof, e.g., one or more of an epitope of interest from a pathogen, e.g., an epitope, antigen or gene product which modifies allergic response, an epitope antigen or gene product which modifies physiological function, influenza hemagglutinin, influenza nuclear protein, influenza M2, tetanus toxin C-fragment, anthrax protective antigen, anthrax lethal factor, rabies glycoprotein, HBV surface antigen, HIV gp 120, HIV gp 160, human carcinoembryonic antigen, malaria CSP, malaria SSP, malaria MSP, malaria pfg, and mycobacterium tuberculosis HSP; and/or a therapeutic or an immunomodulatory gene, a co-stimulatory gene and/or a cytokine gene.

Even further, the invention relates to such methods wherein the immune response can be induced by the vector expressing the nucleic acid molecule in the animal's cells, e.g., epidermal cells. The invention still further relates to such methods wherein the immune response can be against a pathogen or a neoplasm.

Also, the invention relates to compositions used in the methods. For instance, the invention relates to a prophylactic vaccine or a therapeutic vaccine or an immunological composition comprising the vector.

The invention additionally relates to such methods and compositions therefor wherein the animal can be a vertebrate, e.g., a fish, bird, reptile, amphibian or mammal, advantageously a mammal such as a human or a companion or domesticated or food-or feed-producing or livestock or game or racing or sport animal, for instance, a cow, a horse, a dog, a cat, a goat, a sheep or a pig, or fowl such as chickens, duck, turkey.

The invention further relates to such methods and compositions therefor wherein the vector can be one or more of a viral, including viral coat, e.g., with some or all viral genes deleted therefrom, bacterial, protozoan, transposon, retrotransposon, and DNA vector, e.g., a recombinant vector; an adenovirus, such as an adenovirus defective in its E1 and/or E3 and/or E4 region(s).

The invention further relates to mucosal, e.g., intranasal, perlingual, buccal, oral, oral cavity, administration of adenovirus defective in its E1 and/or E3 and E4 region(s), advantageously defective in its E1 and E3 regions, e.g., such an adenovirus comprising an exogenous or heterologous nucleic acid molecule, such as an exogenous or heterologous nucleic acid molecule encoding an epitope of interest of an influenza, e.g., one or more influenza epitiopes of interest and/or one or more influenza antigens. Such an administration can be a method to induce an immunological response, such as a protective immunological response. The adenovirus in this instance can be a human adenovirus. The adenovirus can be another type of adenovirus, such as a canine adenovirus. Thus, if the host or animal is other than a human, the adenovirus can be matched to the host; for example, in veterinary applications wherein the host or animal is a canine such as a dog, the adenovirus can be a canine adenovirus.

The invention accordingly further relates to methods of the invention wherein the vector can be matched to the host or can be a vector that is interesting to employ with respect to the host or animal because the vector can express both heterologous or exogenous and homologous gene products of interest in the animal; for instance, in veterinary applications, it can be useful to use a vector pertinent to the animal, for example, in canines one may use canine adenovirus; or more generally, the vector can be an attenuated or inactivated pathogen of the host or animal upon which the method is being performed.

The invention still further relates to such methods encompassing applying a delivery device including the vector to the skin of the animal, as well as such a method further including disposing the vector in and/or on the delivery device; and, to such delivery devices.

The invention yet further relates to such methods wherein the vector can have all viral genes deleted therefrom, as well as to such vectors.

The invention even further still relates to such methods wherein the vector can induce an anti-tumor effect in the animal, e.g., by expressing an oncogene, a tumor-suppressor gene, or a tumor-associated gene.

In addition, the invention relates to immunological products generated by the expression, cells from the methods, and the expression products, as well as in vitro and ex vivo uses thereof.

BACKGROUND OF THE INVENTION

Activation of the immune system of vertebrates is an important mechanism for protecting animals against pathogens and malignant tumors. The immune system consists of many interacting components including the humoral and cellular branches. Humoral immunity involves antibodies that directly bind to antigens. Antibody molecules as the effectors of humoral immunity are secreted by B lymphocytes. Cellular immunity involves specialized cytotoxic T lymphocytes (CTLs) which recognize and kill other cells which produce non-self antigens. CTLs respond to degraded peptide fragments that appear on the surface of the target cell bound to MHC (major histocompatibility complex) class I molecules. It is understood that proteins produced within the cell are continually degraded to peptides as part of cellular metabolism. These fragments are bound to the MHC molecules and are transported to the cell surface. Thus the cellular immune system is constantly monitoring the spectra of proteins produced in all cells in the body and is poised to eliminate any cells producing non-self antigens.

Vaccination is the process of priming an animal for responding to an antigen. The antigen can be administered as a protein (classical) or as a gene which then expresses the antigen (genetic immunization). The process involves T and B lymphocytes, other types of lymphoid cells, as well as specialized antigen presenting cells (APCs) which can process the antigen and display it in a form which can activate the immune system. Current modes for the administration of genetic vaccines has focused on invasive procedures including needle injections, scarification, and gene gun-mediated penetration. Inoculation of vaccines in an invasive mode requires equipment and personnel with special medical training, and is usually associated with discomfort and potential hazards (bleeding, infection).

The efficacy of a vaccine is measured by the extent of protection against a later challenge by a tumor or a pathogen. Effective vaccines are immunogens that can induce high titer and long-lasting protective immunity for targeted intervention against diseases after a minimum number of inoculations. For example, genetic immunization is an approach to elicit immune responses against specific proteins by expressing genes encoding the proteins in an animal's own cells. The substantial antigen amplification and immune stimulation resulting from prolonged antigen presentation in vivo can induce a solid immunity against the antigen. Genetic immunization simplifies the vaccination protocol to produce immune responses against particular proteins because the often difficult steps of protein purification and combination with adjuvant, both routinely required for vaccine development, are eliminated. Since genetic immunization does not require the isolation of proteins, it is especially valuable for proteins that may lose conformational epitopes when purified biochemically. Genetic vaccines may also be delivered in combination without eliciting interference or affecting efficacy (Tang et al., 1992; Barry et al., 1995), which may simplify the vaccination scheme against multiple antigens.

While topically-applied protein-based vaccines have been studied, their usefulness may be limited. Although topical application of protein-based vaccines in conjunction with cholera toxin may also immunize animals in a non-invasive mode (Glenn et al., 1998), skin-targeted non-invasive genetic vaccines as in the present invention activate the immune system via a different mechanism than protein-based vaccines. Further, the efficacy of genetic vaccines is in general superior to that of protein vaccines due to the de novo synthesis of antigens similar to natural infections (McDonnell and Askari, 1996). Although U.S. Pat. No. 3,837,340 relates to a method for vaccinating animals by contacting skin with dried viruses, the viruses that are employed therein are not genetic vectors capable of expressing transgenes or heterologous or exogenous nucleic acid molecules. In addition, the immunogen may be protein in the viral coat, instead of protein produced from expression of viral genes in the animals's own cells, e.g., any immunological response induced by U.S. Pat. No. 3,837,340 can be akin to that which is induced by topical application of protein-based vaccines which are non-analogous to the present invention and ergo U.S. Pat. No. 3,837,340 is non-analogous to the present invention.

The prior art of vaccination usually requires equipment, e.g., syringe needles or a gene gun, and special skill for the administration of vaccines. There is a great need and desire in the art for the inoculation of vaccines by personnel without medical training and equipment. A large number of diseases could potentially be immunized against through the development of non-invasive vaccination onto the skin (NIVS) because the procedure is simple, effective, economical, painless, and potentially safe. As a consequence, NIVS may boost vaccine coverages in developing countries where medical resources are in short supply, as well as in developed countries due to patient comfort. Infectious diseases caused by viruses, including AIDS and flu, by bacteria, including tetanus and TB, and by parasites, including malaria, and malignant tumors including a wide variety of cancer types may all be prevented or treated with skin-targeted non-invasive vaccines without requiring special equipment and medical personnel. The present invention addresses this longstanding need and desire in the art.

OBJECTS AND SUMMARY OF THE INVENTION

Non-invasive vaccination onto the skin SHIVS) can improve vaccination schemes because skin is an immunocompetent tissue and this non-invasive procedure requires no specially trained personnel. Skin-targeted non-invasive gene delivery can achieve localized transgene expression in the skin and the elicitation of immune responses (Tang et al., 1997) and the mechanism for these responses is different than that from topical application of protein-based vaccines in conjunction with cholera toxin (Glenn et al., 1998). These results indicate that vector-based NIVS is a novel and efficient method for the delivery of vaccines. The simple, effective, economical and painless immunization protocol of the present invention should make vaccination less dependent upon medical resources and, therefore, increase the annual utilization rate of vaccinations.

Accordingly, an object of the invention can be any one or more of: providing a method for inducing an immunological response, e.g., protective immunological response, and/or a therapeutic response in a host or animal, e.g., vertebrate such as mammal, comprising topically administering a vector that comprises and expresses a nucleic acid molecule encoding a gene product that induces or stimulates the response; such a method wherein the nucleic acid molecule is heterologous and/or exogenous with respect to the host; mucosal, e.g., intranasal, perlingual, buccal, oral, oral cavity administration of adenovirus defective in its E1 and/or E3 and/or E4 region(s), advantageously defective in its E1 and E3 and E4 regions, e.g., such an adenovirus comprising an exogenous or heterologous nucleic acid molecule, such as an exogenous or heterologous nucleic acid molecule encoding an epitope of interest of an influenza, e.g., one or more influenza epitiopes of interest and/or one or more influenza antigens; such an administration wherein an immunological response, such as a protective immunological response is induced; products for performing such methods; products from performing such methods; uses for such methods and products, inter alia.

The present invention provides a method of non-invasive genetic immunization in an animal, comprising the step of: contacting skin of the animal with a genetic vector in an amount effective to induce immune response in the animal. The invention also provides a method for immunizing animals comprising the step of skin-targeted non-invasive delivery of a preparation comprising genetic vectors, whereby the vector is taken up by epidermal cells and has an immunogenic effect on vertebrates. The invention further provides a method for immunizing animals by a delivery device, comprising the steps of including genetic vectors in the delivery device and contacting the naked skin of a vertebrate with a uniform dose of genetic material confined within the device, whereby the vector is taken up by epidermal cells for expressing a specific antigen in the immunocompetent skin tissue. The genetic vector may be adenovirus recombinants, DNA/adenovirus complexes, DNA/liposome complexes, or any other genetic vectors capable of expressing antigens in the skin of a vertebrate.

In an embodiment of the present invention, there is provided a method of inducing an immune response, comprising the step of: contacting skin of an individual or animal in need of such treatment by topically applying to said skin an immunologically effective concentration of a genetic vector encoding a gene of interest.

In another embodiment of the present invention, there is provided a method of inducing a protective immune response in an individual or animal in need of such treatment, comprising the step of: contacting the skin of said animal by topically applying to said skin an immunologically effective concentration of a vector encoding a gene which encodes an antigen which induces a protective immune effect in said individual or animal following administration.

In another embodiment, the invention presents a method for co-expressing transgenes in the same cell by contacting naked skin with DNA/adenovirus complexes. This protocol may allow the manipulation of the immune system by co-producing cytokines, costimulatory molecules, or other immune modulators with antigens within the same cellular environment.

The invention thus provides methods of non-invasive genetic immunization in an animal and/or methods of inducing an immune, e.g., systemic immune, or therapeutic response in an animal, products therefrom and uses for the methods and products therefrom. The invention further provides such methods comprising contacting skin of the animal with a vector in an amount effective to induce the response, e.g., immune response such as systemic immune response or therapeutic response, in the animal. Even further, the invention provides such methods wherein the vector comprises and expresses an exogenous nucleic acid molecule encoding an epitope or gene product of interest. Still further, the invention provides such methods wherein the systemic immune response can be to or from the epitope or gene product.

The invention yet further still provides such methods wherein the nucleic acid molecule can encode an epitope of interest and/or an antigen of interest and/or a nucleic acid molecule that stimulates and/or modulates an immunological response and/or stimulates and/or modulates expression, e.g., transcription and/or translation, such as transcription and/or translation of an endogenous and/or exogenous nucleic acid molecule; and/or elicits a therapeutic response.

The invention additionally provides such methods wherein the nucleic acid molecule can be exogenous to the vector. The invention also provides such methods wherein the exogenous nucleic acid molecule encodes one or more of an antigen of interest or portion thereof, e.g., an epitope of interest, from a pathogen; for instance, one or more of an epitope of interest from or the antigen comprising influenza hemagglutinin, influenza nuclear protein, influenza M2, tetanus toxin C-fragment, anthrax protective antigen, anthrax lethal factor, rabies glycoprotein, HBV surface antigen, HIV gp 120, HIV gp 160, human carcinoembryonic antigen, malaria CSP, malaria SSP, malaria MSP, malaria pfg, and mycobacterium tuberculosis HSP; and/or a therapeutic and/or an immunomodulatory gene, such as a co-stimulatory gene and/or a cytokine gene. See also U.S. Pat. No. 5,990,091, WO 99/60164 and WO 98/00166 and documents cited therein.

Even further, the invention provides such methods wherein the immune response can be induced by the vector expressing the nucleic acid molecule in the animal's cells, e.g., epidermal cells. The invention still further provides such methods wherein the immune response can be against a pathogen or a neoplasm.

Also, the invention provides compositions used in the methods. For instance, the invention provides a prophylactic vaccine or a therapeutic vaccine or an immunological or a therapeutic composition comprising the vector, e.g., for use in inducing or stimulating a response via topical application and/or via mucosal and/or nasal and/or perlingual and/or buccal and/or oral and/or oral cavity administration.

The invention additionally provides to such methods and compositions therefor wherein the animal can be a vertebrate, e.g., a fish, amphibian, reptile, bird, or mammal, such as human, or a domesticated or companion or feed-producing or food-producing or livestock or game or racing or sport animal such as a cow, a dog, a cat, a goat, a sheep, a horse, or a pig; or, fowl such as turkeys, ducks and chicken.

The invention further provides such methods and compositions therefor wherein the vector can be one or more of a viral, including viral coat, e.g., with some or all viral genes deleted therefrom, bacterial, protozoan, transposon, retrotransposon, and DNA vector, e.g., a recombinant vector; an adenovirus, such as an adenovirus defective in its E1 and/or E3 and/or E4 region(s).

The invention further provides intranasal and/or mucosal and/or perlingual and/or buccal and/or oral and/or oral cavity administration of adenovirus defective in its E1 and/or E3 and/or E4 region(s), advantageously defective in its E1 and E3 and E4 regions, e.g., such an adenovirus comprising an exogenous or heterologous nucleic acid molecule, such as an exogenous or heterologous nucleic acid molecule encoding an epitope of interest of an influenza, e.g., one or more influenza epitiopes of interest and/or one or more influenza antigens. Such an administration can be a method to induce an immunological response, such as a protective immunological response. The adenovirus in this instance can be a human adenovirus. The adenovirus can be another type of adenovirus, such as a canine adenovirus. Thus, if the host or animal is other than a human, the adenovirus can be matched to the host; for example, in veterinary applications wherein the host or animal is a canine such as a dog, the adenovirus can be a canine adenovirus.

The invention accordingly further relates to methods of the invention wherein the vector can be matched to the host or can be a vector that is interesting to employ with respect to the host or animal because the vector can express both heterologous or exogenous and homologous gene products of interest in the animal; for instance, in veterinary applications, it can be useful to use a vector pertinent to the animal, for example, in canines one may use canine adenovirus; or more generally, the vector can be an attenuated or inactivated natural pathogen of the host or animal upon which the method is being performed. One skilled in the art, with the information in this disclosure and the knowledge in the art, can match a vector to a host or animal without undue experimentation.

The invention still further provides such methods encompassing applying a delivery device including the vector to the skin of the animal, as well as such a method further including disposing the vector in and/or on the delivery device; and, to such delivery devices.

The invention yet further provides such methods wherein the vector can have all viral genes deleted therefrom, as well as to such vectors.

The invention even further still provides such methods wherein the vector can induce a therapeutic effect, e.g., an anti-tumor effect in the animal, for instance, by expressing an oncogene, a tumor-suppressor gene, or a tumor-associated gene.

In addition, the invention provides gene products, e.g., expression products, as well as immunological products (e.g., antibodies), generated by the expression, cells from the methods, as well as in vitro and ex vivo uses thereof. The expression products and immunological products therefrom may be used in assays, diagnostics, and the like; and, cells that express the immunological products and/or the expression products can be isolated from the host, expanded in vitro and re-introduced into the host.

Even further still, while non-invasive delivery is desirable in all instances of administration, the invention can be used in conjunction with invasive deliveries; and, the invention can generally be used as part of a prime-boost regimen. For instance, the methods of the present invention can be used a part of a prime-boost regimen wherein the non-invasive inventive method is administered prior to or after or concurrently with another administration such as another non-invasive or an invasive administration of the same or a different immunological or therapeutic ingredient, e.g., before, during or after the non-invasive administration, there is administration by injection of a different vaccine or immunological composition for the same or similar pathogen such as a whole or subunit vaccine or immunological composition for the same or similar pathogen whose antigen or epitope of interest is expressed by the vector in the non-invasive administration.

The present invention also encompasses delivery devices (bandages, adhesive dressings, spot-on formulation and its application devices, pour-on formulation and its application devices, roll-on formulation and its application devices, shampoo formulation and its application devices or the like) for the delivery of skin-targeted and other non-invasive vaccines or immunological compositions and uses thereof, as well as compositions for the non-invasive delivery of vectors; and, kits for the preparation of compositions for the non-invasive delivery of vectors. Such a kit comprises the vector and a pharmaceutically acceptable or suitable carrier or diluent and an optional delivery device, each in its own packaging; the packaging may be included in a unitary container or the packaging may each be in separate containers or each may be its own separate container; the kit can optionally include instructions for admixture of the ingredients and/or administration of the composition.

Pour-on and spot-on formulations are described in U.S. Pat. Nos. 6,010,710 and 5,475,005. A roll-on device is also described in U.S. Pat. No. 5,897,267. The contents of U.S. Pat. Nos. 6,010,710, 5,475,005 and 5,897,267 are hereby incorporated herein by reference, together with documents cited or referenced therein and all documents cited or referenced in such documents. Moreover, a skilled artisan also knows make shampoo formulation as well as devices to apply the formulation to an animal.

Thus, the present invention also includes all genetic vectors for all of the uses contemplated in the methods described herein.

It is noted that in this disclosure, terms such as "comprises", "comprised", "comprising" and the like can have the meaning attributed to it in U.S. Patent law; e.g., they can mean "includes", "included", "including" and the like.

These and other embodiments are disclosed or are obvious from and encompassed by, the following Detailed Description.

BRIEF DESCRIPTION OF FIGURES

The following Detailed Description, given by way of example, but not intended to limit the invention to specific embodiments described, may be understood in conjunction with the accompanying Figures, incorporated herein by reference, in which:

FIG. 1 shows the transgene expression from adenovirus recombinants in the skin by topical application of the vectors;

DETAILED DESCRIPTION

Figure 2A:
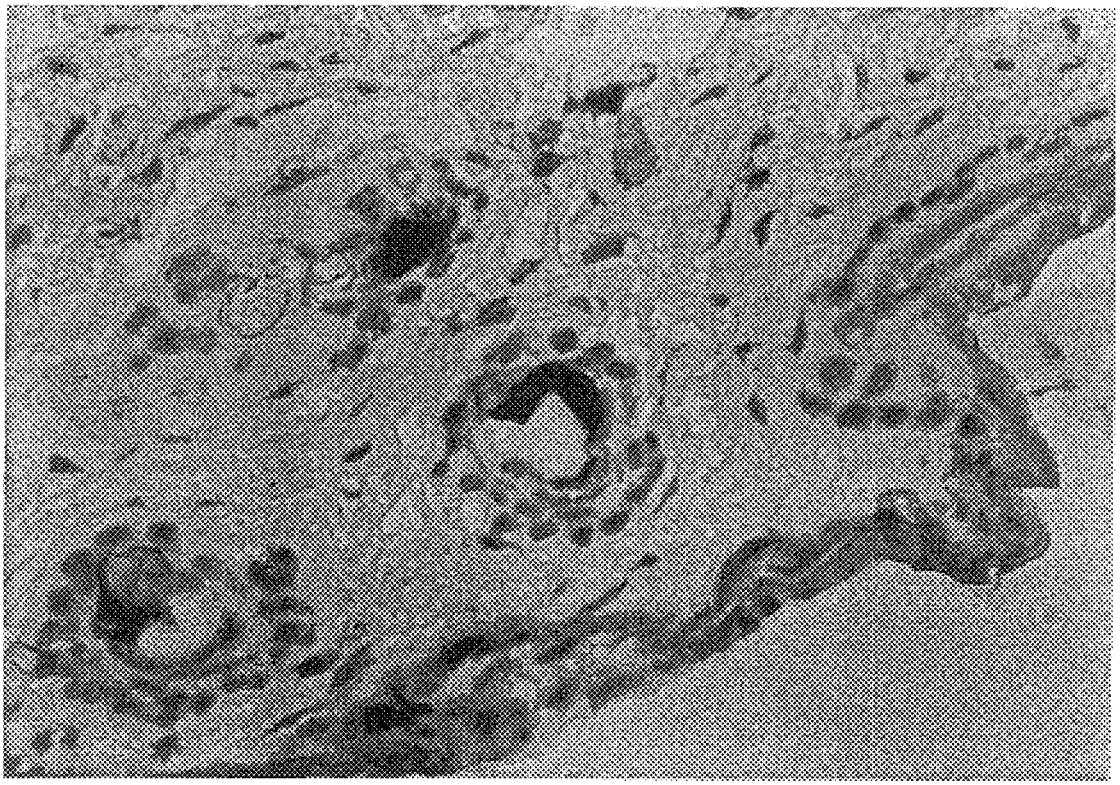
FIGS. 2a and 2b show the characterization of potential target cells that can be transduced by topically-applied adenovirus recombinants.

Inoculation of vaccines in an invasive mode may be unnecessary (Tang et al., 1997; Glenn et al., 1998). Since the skin interfaces directly with the external environment and is in constant contact with potential pathogens, the immune system must constantly keep a mobilized biological army along the skin border for warding off potential infections. As a consequence, the outer layer of skin is essentially an immunocompetent tissue. Immunologic components present in the skin for the elicitation of both humoral and cytotoxic cellular immune responses include epidermal Langerhans cells (which are MHC class II-positive antigen-presenting cells), keratinocytes, and both $CD4^+$ and $CD8^+T$ lymphocytes. These components make the skin an ideal site for administration of vaccine. The large accessible area of skin and its durability are other advantages for applying vaccines to this tissue. Expression of a small number of antigens in the outer layer of skin without physical penetration may thus elicit a potent immune response by alarming the immune surveillance mechanism.

It is herein demonstrated that genetic vaccines can be inoculated in a novel way as skin-targeted non-invasive vaccine, or immunogenic, or immunological or therapeutic compositions. The combination of genetic vaccines with a non-invasive delivery mode results in a new class of "democratic" vaccine, or immunogenic, or immunological or therapeutic compositions that require may require little or no special skill and equipment for administration. Thus, one can administer such compositions to the skin of himself or herself (and, this administration can advantageously be under the direction of a medical practitioner, e.g., to ensure that dosage is proper) or to the skin of an animal (e.g., advantageously a shaved area of skin if the animal is a mammal, although as demonstrated herein, hair removal is not necessary, and more advantageously at a region where the animal will not remove the administration by rubbing, grooming or other activity); and, the present invention thus provides advantages in the administration of vaccine, or immunogenic, or immunological, or therapeutic compositions comprising a vector that expresses a gene product, especially with respect to administering such compositions to newborns, young animals, animals generally, children and the like, to whom invasive, e.g., needle, administration may be somewhat difficult or inconvenient or painful.

The present invention is directed to a method of non-invasive genetic immunization or treatment in an animal, comprising the step of: contacting skin of the animal with a genetic vector in an amount effective to induce immune response in the animal.

As used herein, a vector is a tool that allows or facilitates the transfer of an entity from one environment to another. By way of example, some vectors used in recombinant DNA techniques allow entities, such as a segment of DNA (such as a heterologous DNA segment, such as a heterologous cDNA segment), to be transferred into a target cell. In an advantageous embodiment, the vector includes a viral vector, a bacterial vector, a protozoan vector, a DNA vector, or a recombinant thereof.

As used herein, "AdCMV-tetC:IM" represents an adenovirus vector encoding the *Clotridium tetani* toxin C-fragment; "pCMV-tetC" represents a plasmid expression vector a encoding the *Clotridium tetani* toxin C-fragment.

Reference is made to U.S. Pat. No. 5,990,091 issued Nov. 23, 1999, Einat et al. or Quark Biotech, Inc., WO 99/60164, published Nov. 25, 1999 from PCT/US99/11066, filed May 14, 1999, Fischer or Rhone Merieux, Inc., WO 098/00166, published Jan. 8, 1998 from PCTUS97/11486, filed Jun. 30, 1997 (claiming priority from U.S. applications Ser. Nos. 08/675,556 and 08/675,566), van Ginkel et al., J. Immunol 159(2):685–93 (1997) ("Adenoviral gene delivery elicits distinct pulmonary-associated T helper cell responses to the vector and to its transgene"), Osterhaus et al., Immunobiology 184(2–3):180–92 (1992) ("Vaccination against acute respiratory virus infections and measles in man"), Briles et al. or UAB, WO 99/53940, published Oct. 28, 1999 from PCT/US99/08895, filed Apr. 23, 1999, and Briles et al. or UAB, U.S. Pat. No. 6,042,838, issued Mar. 28, 2000, and Briles et al. or UAB U.S. Pat. No. 6,004,802, for information concerning expressed gene products, antibodies and uses thereof, vectors for in vivo and in vitro expression of exogenous nucleic acid molecules, promoters for driving expression or for operatively linking to nucleic acid molecules to be expressed, method and documents for producing such vectors, compositions comprising such vectors or nucleic acid molecules or antibodies, dosages, and modes and/or routes of administration (including compositions for mucosal, nasal, oral, oral cavity, buccal, perlingual administration), inter alia, which can be employed in the practice of this invention; and thus, U.S. Pat. No. 5,990,091 issued Nov. 23, 1999, Einat et al. or Quark Biotech, Inc., WO 99/60164, published Nov. 25, 1999 from PCT/US99/11066, filed May 14, 1999, Fischer or Rhone Merieux, Inc., WO 098/00166, published Jan. 8, 1998 from PCT/US97/11486, filed Jun. 30, 1997 (claiming priority from U.S. applications Ser. Nos. 08/675,556 and 08/675,566), van Ginkel et al., J. Immunol 159(2):685–93 (1997) ("Adenoviral gene delivery elicits distinct pulmonary-associated T helper cell responses to the vector and to its transgene"), Osterhaus et al., Immunobiology 184(2–3):180–92 (1992) ("Vaccination against acute respiratory virus infections and measles in man"), Briles et al. or UAB, WO 99/53940, published Oct. 28, 1999 from PCTIUS99/08895, filed Apr. 23, 1999, and Briles et al. or UAB, U.S. Pat. No. 6,042,838, issued March 28, 2000 and Briles et al. or UAB, U.S. Pat. No. 6,004,802, and all documents cited or referenced therein and all documents cited or referenced in documents referenced or cited in each of U.S. Pat. No. 5,990,091 issued Nov. 23, 1999, Einat et al. or Quark Biotech, Inc., WO 99/60164, published Nov. 25, 1999 from PCT/US99/11066, filed May 14, 1999, Fischer or Rhone Merieux, Inc., WO 098/00166, published Jan. 8, 1998 from PCTIUS97/11486, filed Jun. 30, 1997 (claiming priority from U.S. applications Ser. Nos. 08/675,556 and 08/675,566), van Ginkel et al., J. Immunol 159(2):685–93 (1997) ("Adenoviral gene delivery elicits distinct pulmonary-associated T helper cell responses to the vector and to its transgene"), Osterhaus et al., Immunobiology 184(2–3):180–92 (1992) ("Vaccination against acute respiratory virus infections and measles in man"), Briles et al. or UAB, WO 99/53940, published Oct. 28, 1999 from PCT/US99/08895, filed Apr. 23, 1999, and Briles et al. or UAB, U.S. Pat. No. 6,042,838, issued March 28, 2000, and Briles et al. or UAB U.S. Pat. No. 6,004,802, are hereby incorporated herein by reference. Information in U.S. Pat. No. 5,990,091 issued Nov. 23, 1999, WO 99/60164, WO 098/00166, van Ginkel et al., J. Immunol 159(2):685–93 (1997), Osterhaus et al., Immunobiology 184(2–3): 180–92 WO 99/53940 and U.S. Pat. Nos. 6,042,838 and 6,004,802, can be relied upon for the practice of this invention (e.g., expressed products, antibodies and uses thereof, vectors for in vivo and in vitro expression of exogenous nucleic acid molecules, exogenous nucleic acid molecules encoding epitopes of interest or antigens or therapeutics and the like, promoters, compositions comprising such vectors or nucleic acid molecules or expressed products or antibodies, dosages, inter alia). It is noted that immunological products and/or antibodies and/or expressed products obtained in accordance with this invention can be expressed in vitro and used in a manner in which such immunological and/or expressed products and/or antibodies are typically used, and that cells that express such immunological and/or expressed products and/or antibodies can be employed in vitro and/or ex vivo applications, e.g., such uses and applications can include diagnostics, assays, ex vivo therapy (e.g., wherein cells that express the gene product and/or immunological response are expanded in vitro and reintroduced into the host or animal), etc., see U.S. Pat. No. 5,990,091, WO 99/60164, WO 98/00166, WO 99/53940, and U.S. Pat. Nos. 6,042,838, and 6,004,802, and documents cited therein and documents cited or referenced in such documents. Further, expressed antibodies or gene products that are isolated from herein methods, or that are isolated from cells expanded in vitro following herein administration methods, can be administered in compositions, akin to the administration of subunit epitopes or antigens or therapeutics or antibodies to induce inmmunity, stimulate a therapeutic response and/or stimulate passive immunity. The quantity to be administered will vary for the patient (host) and condition being treated and will vary from one or a few to a few hundred or thousand micrograms, e.g., 1 μg to 1 mg, from about 100 ng/kg of body weight to 100 mg/kg of body weight per day and preferably will be from 10 pg/kg to 10 mg/kg per day. A vector can be non-invasively administered to a patient or host in an amount to achieve the amounts stated for gene product (e.g., epitope, antigen, therapeutic, and/or antibody) compositions. Of course, the invention envisages dosages below and above those exemplified herein, and for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response, such as by titrations of sera and analysis thereof, e.g., by ELISA and/or seroneutralization analysis. Such determinations do not require undue experimentation from the knowledge of the skilled artisan, this disclosure and the documents cited herein. And, the invention also comprehends sequential administration of inventive compositions or sequential performance of herein methods, e.g., periodic administration of inventive compositions such as in the course of therapy or treatment for a condition and/or booster administration of immunological compositions and/or in prime-boost regimens; and, the time and manner for sequential administrations can be ascertained without undue experimentation. Further, the invention comprehends compositions and methods for making and using vectors, including methods for producing gene products and/or immunological products and/or antibodies in vivo and/or in vitro and/or ex vivo (e.g., the latter two being, for instance, after isolation therefrom from cells from a host that has had a non-invasive administration according to the invention, e.g., after optional expansion of such cells), and uses for such gene and/or immunological products and/or antibodies, including in diagnostics, assays, therapies, treatments, and the like. Vector compositions are formulated by admixing the vector with a suitable carrier or diluent; and, gene product and/or immunological product and/or antibody compositions are likewise formulated by admixing the gene and/or immunological product and/or antibody with a suitable carrier or diluent; see, e.g., U.S. Pat. No. 5,990,091, WO 99/60164, WO 98/00166, WO 99/53940, and U.S. Pat. Nos. 6,042,838 and 6,004,802, documents cited therein, and other documents cited herein, and other teachings herein (for instance, with respect to carriers, diluents and the like).

If nasal or respiratory (mucosal) administration is desired, compositions may be in a form and dispensed by a squeeze spray dispenser, pump dispenser or aerosol dispenser. Such dispensers may also be employed to deliver the composition to oral or oral cavity (e.g., buccal or perlingual) mucosa. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally (or buccally or perlingually); and, such compositions can be in the form of tablets or capsules that dissolve in the mouth or which are bitten to release a liquid for absorption buccally or perlingually (akin to oral, perlingual or buccal medicaments for angina such as nitroglycerin or nifedimen). The viscous compositions may be in the form of gels, lotions, ointments, creams and the like (e.g., for topical and/or mucosal and/or nasal and/or oral and/or oral cavity and/or perlingual and/or buccal administration), and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion and/or a pill or capsule or tablet for holding in the mouth, e.g., for buccal or perlingual administration.

Liquid preparations are normally easier to prepare than gels, other viscous compositions, and solid compositions. Additionally, liquid compositions are somewhat more convenient to administer, especially by injection or orally or buccally or perlinually, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa or for perlingual or buccal or oral cavity absorption.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigen, lipoprotein and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the vector or antigen or epitope of interest and optional adjuvant or other active or immunity-enhancing ingredients. This will present no problem to those skilled in chemical and pharmaceutical principles, or problems can be readily avoided by reference to standard texts or by simple experiments (not involving undue experimentation), from this disclosure and the documents cited herein.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity.

Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other mammals can be determined without undue experimentation by the skilled artisan, from this disclosure, the documents cited herein, the Examples below and from the applications, patents and other documents cited herein and documents cited or referenced in documents cited herein, all of which are incorporated herein by reference.

Suitable regimes for initial administration and booster doses or for sequential administrations also are variable, and may include an initial administration followed by subsequent administrations; but nonetheless, may be ascertained by the skilled artisan, from this disclosure, the documents cited and incorporated by reference herein, including applications and patents cited herein and documents referenced or cited in herein cited documents, all of which are hereby incorporated herein by reference, as well as the Examples below. The compositions can be administered alone, or can be co-administered or sequentially administered with other compositions of the invention or with other prophylactic or therapeutic compositions.

In another advantageous embodiment, the vector expresses a gene which encodes influenza hemagglutinin, influenza nuclear protein, influenza M2, tetanus toxin C-fragment, anthrax protective antigen, anthrax lethal factor, rabies glycoprotein, HBV surface antigen, HIV gp 120, HIV gp 160, human carcinoembryonic antigen, malaria CSP, malaria SSP, malaria MSP, malaria pfg, mycobacterium tuberculosis HSP or a mutant thereof.

In an embodiment of the invention, the immune response in the animal is induced by genetic vectors expressing genes encoding antigens of interest in the animal's cells. In another embodiment of the invention, the antigen of interest is selected from the group comprising influenza hemagglutinin, influenza nuclear protein, influenza M2, tetanus toxin C-fragment, anthrax protective antigen, anthrax lethal factor, rabies glycoprotein, HBV surface antigen, HIV gp 120, HIV gp 160, human carcinoembryonic antigen, malaria CSP, malaria SSP, malaria MSP, malaria pfg, and mycobacterium tuberculosis HSP. In another embodiment of the method, the animal's cells are epidermal cells. In another embodiment of the method, the immune response is against a pathogen or a neoplasm. In another embodiment of the method, the genetic vector is used as a prophylactic vaccine or a therapeutic vaccine. In another embodiment of the invention, the genetic vector comprises genetic vectors capable of expressing an antigen of interest in the animal's cells. In a further embodiment of the method, the animal is a vertebrate.

With respect to exogenous DNA for expression in a vector (e.g., encoding an epitope of interest and/or an antigen and/or a therapeutic) and documents providing such exogenous DNA, as well as with respect to the expression of transcription and/or translation factors for enhancing expression of nucleic acid molecules, and as to terms such as "epitope of interest", "therapeutic", "immune response", "immunological response", "protective immune response", "immunological composition", "immunogenic composition", and "vaccine composition", inter alia, reference is made to U.S. Pat. No. 5,990,091 issued Nov. 23, 1999, and WO 98/00166 and WO 99/60164, and the documents cited therein and the documents of record in the prosecution of that patent and those PCT applications; all of which are incorporated herein by reference. Thus, U.S. Pat. No. 5,990,091 and WO 98/00166 and WO 99/60164 and documents cited therein and documents or record in the prosecution of that patent and those PCT applications, and other documents cited herein or otherwise incorporated herein by reference, can be consulted in the practice of this invention; and, all exogenous nucleic acid molecules, promoters, and vectors cited therein can be used in the practice of this invention. In this regard, mention is also made of U.S. Pat. Nos. 6,004,777, 5,997,878, 5,989,561, 5,976,552, 5,972,597, 5,858,368, 5,863,542, 5,833,975, 5,863,542, 5,843,456, 5,766,598, 5,766,597, 5,762,939, 5,756,102, 5,756,101, 5,494,807, 6,042,838, 6,004,802 and WO 99/53940.

In another embodiment of the invention, the animal is advantageously a vertebrate such as a mammal, bird, reptile, amphibian or fish; more advantageously a human, or a companion or domesticated or food-producing or feed-producing or livestock or game or racing or sport animal such as a cow, a dog, a cat, a goat, a sheep or a pig or a horse, or even fowl such as turkey, ducks or chicken. In an especially advantageous another embodiment of the invention, the vertebrate is a human. In another embodiment of the invention, the genetic vector is a viral vector, a bacterial vector, a protozoan vector, a retrotransposon, a transposon, a virus shell, or a DNA vector. In another embodiment of the invention, the viral vector, the bacterial vector, the protozoan vector and the DNA vector are recombinant vectors. In another embodiment of the invention, the immune response is against influenza A. In another embodiment of the invention, the immune response against influenza A is induced by the genetic vector expressing a gene encoding an influenza hemagglutinin, an influenza nuclear protein, an influenza M2 or a fragment thereof in the animal's cells. In another embodiment of the invention, the genetic vector is selected from the group consisting of viral vector and plasmid DNA. In another embodiment of the invention, the genetic vector is an adenovirus. In another embodiment of the invention, the adenovirus vector is defective in its E1 region. In another embodiment of the invention, the adenovirus vector is defective in its E3 region. In another embodiment of the invention, the adenovirus vector is defective in its E1 anld E3 regions. In another embodiment of the invention, the DNA is in plasmid form. In another embodiment of the invention, the contacting step further comprises disposing the genetic vector containing the gene of interest on a delivery device and applying the device having the genetic vector containing the gene of interest therein to the skin of the animal. In another embodiment of the invention, the genetic vector encodes an immunomodulatory gene, a co-stimulatory gene or a cytokine gene. In another embodiment of the invention, the vector has all viral genes deleted. In another embodiment of the invention, the genetic vector induces an anti-tumor effect in the animal. In a further embodiment of the invention, the genetic vector expresses an oncogene, a tumor-suppressor gene, or a tumor-associated gene.

The present invention also provides a method of non-invasive genetic immunization in an animal, comprising the step of: contacting skin of the animal with a genetic vector in an amount effective to induce immune response in the animal.

Representative examples of antigens which can be used to produce an immune response using the methods of the present invention include influenza hemagglutinin, influenza nuclear protein, influenza M2, tetanus toxin C-fragment, anthrax protective antigen, anthrax lethal factor, rabies glycoprotein, HBV surface antigen, HIV gp 120, HIV gp 160, human carcinoembryonic antigen, malaria CSP, malaria SSP, malaria MSP, malaria pfg, and mycobacterium tuberculosis HSP, etc. Most preferably, the immune response produces a protective effect against neoplasms or infectious pathogens.

The practice of the present invention includes delivering genetic vectors operatively coding for a polypeptide into the outer layer of skin of a vertebrate by a non-invasive procedure for immunizing the animal or for administering a therapeutic. These genetic vectors can be administered to the vertebrate by direct transfer of the genetic material to the skin without utilizing any devices, or by contacting naked skin utilizing a bandage or a bandage-like device. In preferred applications, the genetic vector is in aqueous solution. Vectors reconstituted from lyophilized powder are also acceptable. The vector may encode a complete gene, a fragment of a gene or several genes, gene fragments fused with immune modulatory sequences such as ubiquitin or CpG-rich synthetic DNA, together with transcription/translation signals necessary for expression.

In another embodiment of the present invention, the vector further contains a gene selected from the group consisting of co-stimulatory genes and cytokine genes. In this method the gene is selected from the group consisting of a GM-CSF gene, a B7-1 gene, a B7-2 gene, an interleukin-2 gene, an interleukin-12 gene and interferon genes.

In a further embodiment of the present invention, the response is against *Clostridium tetanus* infection or the vector comprises AdCMV-tetC:IM or pCMV-tetC. In still another embodiment of the method, the exogenous nucleic acid molecule encodes tetanus toxin C-fragment, or an antigen or epitope of tetanus toxin.

The present invention also provides for a method of non-invasively inducing an immune response to influenza A virus comprising the step of. contacting skin of a subject in need of such treatment topically by applying to the skin an immunologically effective amount of a genetic vector encoding for influenza-specific antigens or fragments thereof which induce an anti-influenza effect in the animal following administration. In one embodiment of the method, the genetic vector is selected from the group consisting of viral vector and plasmid DNA. In another embodiment of the method, the genetic vector is an adenovirus. In another embodiment of the method, the adenovirus vector is defective in its E1 and E3 regions. In a further embodiment of the method, the DNA is in plasmid form. In still another embodiment of the method, the contacting step further comprises disposing the genetic vector containing the gene of interest on a delivery device and applying the device having the genetic vector containing the gene of interest therein to the skin of the animal.

Embodiments of the invention that employ adenovirus recombinants, may include E1-defective, E3-defective, and/or E4-defective adenovirus vectors, or the "gutless" adenovirus vector in which all viral genes are deleted. The E1 mutation raises the safety margin of the vector because E1-defective adenovirus mutants are replication incompetent in non-permissive cells. The E3 mutation enhances the immunogenicity of the antigen by disrupting the mechanism whereby adenovirus down-regulates MHC class I molecules. The E4 mutation reduces the immunogenicity of the adenovirus vector by suppressing the late gene expression, thus may allow repeated re-vaccination utilizing the same vector. The "gutless" adenovirus vector is the latest model in the adenovirus vector family. Its replication requires a helper virus and a special human 293 cell line expressing both E1a and Cre, a condition that does not exist in natural environment; the vector is deprived of all viral genes, thus the vector as a vaccine carrier is non-immunogenic and may be inoculated for multiple times for re-vaccination. The "gutless" adenovirus vector also contains 36 kb space for accommodating transgenes, thus allowing co-delivery of a large number of antigen genes into cells. Specific sequence motifs such as the RGD motif may be inserted into the H-I loop of an adenovirus vector to enhance its infectivity. An adenovirus recombinant is constructed by cloning specific transgenes or fragments of transgenes into any of the adenovirus vectors such as those described above. The adenovirus recombinant is used to transduce epidermal cells of a vertebrate in a non-invasive mode for use as an immunizing agent.

Embodiments of the invention that use DNA/adenovirus complexes can have the plasmid DNA complexed with adenovirus vectors utilizing a suitable agent therefor, such as either PEI (polyethylenimine) or polylysine. The adenovirus vector within the complex may be either "live" or "killed" by UV or gamma irradiation. The irradiation-inactivated adenovirus vector as a receptor-binding ligand and an endosomolysis agent for facilitating DNA-mediated transfection (Cotten et al., 1992) may raise the safety margin of the vaccine carrier. The DNA/adenovirus complex is used to transfect epidermal cells of a vertebrate in a non-invasive mode for use as an immunizing agent.

Embodiments of the invention that use DNA/liposome complexes can have materials for forming liposomes, and DNA/liposome complexes be made from these materials. The DNA/liposome complex is used to transfect epidermal cells of a vertebrate in a non-invasive mode for use as an immunizing agent.

Genetic vectors provided by the invention can also code for immunomodulatory molecules which can act as an adjuvant to provoke a humoral and/or cellular immune response. Such molecules include cytokines, co-stimulatory molecules, or any molecules that may change the course of an immune response. One can conceive of ways in which this technology can be modified to enhance still further the immunogenicity of antigens.

The genetic vector used for NIVS can take any number of forms, and the present invention is not limited to any particular genetic material coding for any particular polypeptide. All forms of genetic vectors including viral vectors, bacterial vectors, protozoan vectors, transposons, retrotransposons, virus-like-particles, and DNA vectors, when used as skin-targeted non-invasive vaccine carriers, are within the methods contemplated by the invention.

Figure 11:
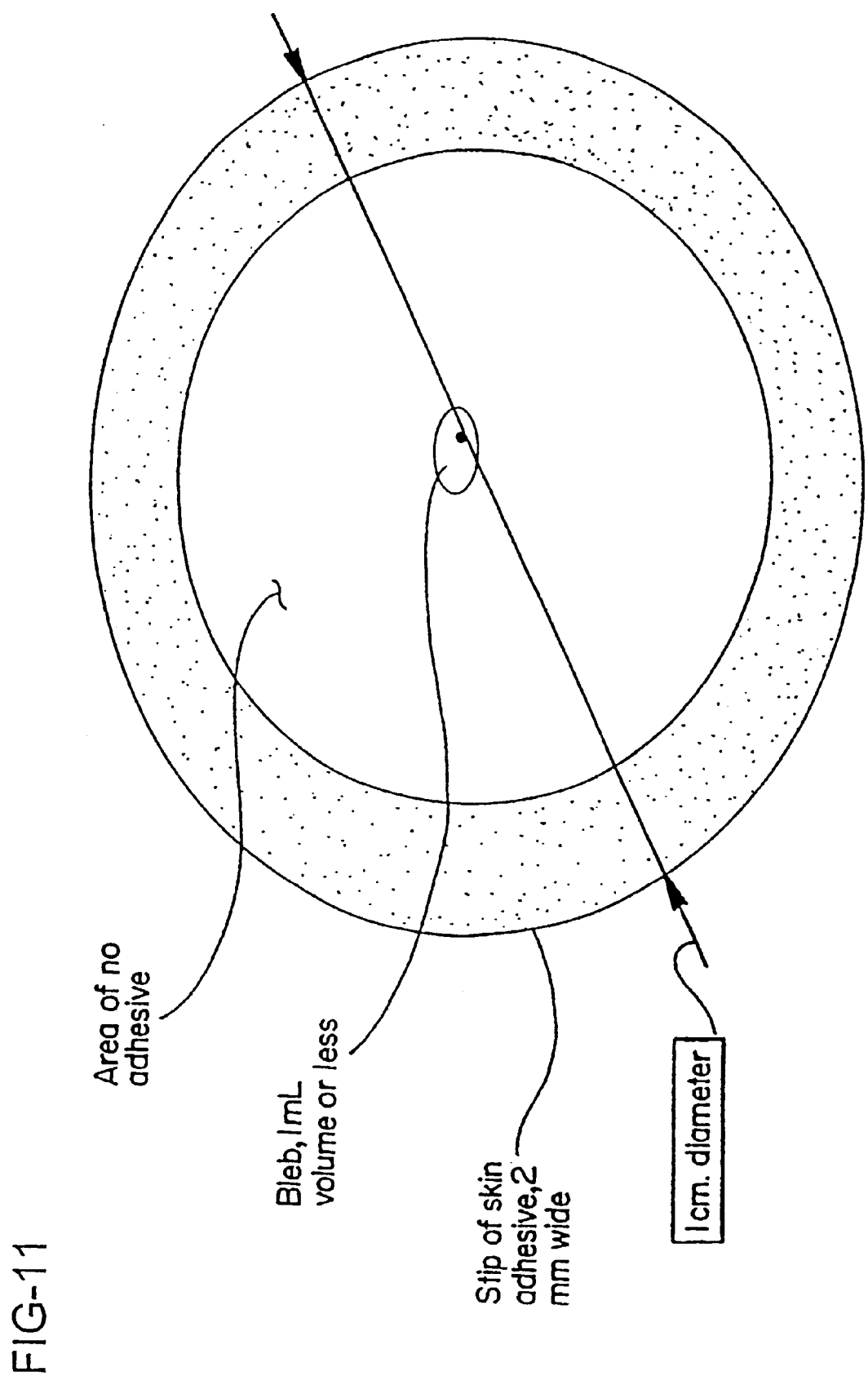
FIG. 11 shows a device for the administration of skin-targeted non-invasive vaccines.

The genes can be delivered by various methods including device-free topical application or coating the genes on the surface of the skin of an animal by a device such as a pad or bandage; e.g., an adhesive bandage. Referring to FIG. 11, a device for non-invasive vaccination is shown. This vaccine delivery device includes a non-allergenic, skin adhesive patch having a bleb disposed therein. In one embodiment, the patch is further comprised of plastic, approximately 1 cm in diameter. The vaccine can be disposed within the bleb. In another embodiment, the bleb contains approximately 1 mL of vaccine (as liquid, lyophilized powder with reconstituting fluid, and variants thereof). In a preferred embodiment, the surface of the bleb in contact with the skin is intentionally weaker than the opposite surface, such that when pressure is applied to the opposite surface, the lower surface breaks and releases the vaccine contents of the bleb onto the skin. The plastic patch traps the vaccine against the skin surface.

Dosage forms for the topical administration of the genetic vector and gene of interest of this invention can include liquids, ointments, powders, and sprays. The active component can be admixed under sterile conditions with a physiologically acceptable carrier and any preservatives, buffers, propellants, or absorption enhancers as may be required or desired. Reference is made to documents cited herein, e.g., U.S. Pat. Nos. 5,990,091, 6,042,838, and 6,004,802, and WO 98/00166 and WO 99/60164, and WO 99/53940, and documents cited therein for methods for constructing vectors, as well as for compositions for topical application, e.g., viscous compositions that can be creams or ointments, as well as compositions for nasal and/or mucosal and/or oral cavity and/or buccal and/or perlingual administration.

In terms of the terminology used herein, an immunologically effective amount is an amount or concentration of the genetic vector encoding the gene of interest, that, when administered to an animal, produces an immune response to the gene product of interest.

Various epitopes, antigens or therapeutics may be delivered topically by expression thereof at different concentrations. Generally, useful amounts for adenovirus vectors are at least approximately 100 pfu and for plasmid DNA at least approximately 1 ng of DNA. Other amounts can be ascertained from this disclosure and the knowledge in the art, including documents cited and incorporated herein by reference, without undue experimentation.

The methods of the invention can be appropriately applied to prevent diseases as prophylactic vaccination or treat diseases as therapeutic vaccination.

The vaccines of the present invention can be administered to an animal either alone or as part of an immunological composition.

Beyond the human vaccines described, the method of the invention can be used to immunize animal stocks. The term animal means all animals including humans. Examples of animals include humans, cows, dogs, cats, goats, sheep, horses, pigs, turkey, ducks and chicken, etc. Since the immune systems of all vertebrates operate similarly, the applications described can be implemented in all vertebrate systems.

The following examples are given for the purpose of illustrating various embodiments of the invention and are not meant to limit the present invention in any fashion.

EXAMPLES

Protocols

Mice and Cell Cultures

Inbred mice were maintained at the University of Alabama at Birmingham. Cells were cultured in RPMI 1640 or DMEM media containing 2% fetal bovine serum and 6% calf serum.

Topical Application of Genetic Vectors

Mice were anesthetized and hair and cornified epithelium covering a restricted area of abdominal or neck skin were removed by a brush or a depilatory (e.g., NAIR). Genetic vectors were pipetted onto the preshaved skin and kept in contact with naked skin for varying amounts of time (e.g., 1 hour to 18 hours). Vectors may be pipetted directly onto naked skin, or into a cylinder that is glued onto the skin.

Preparation of Adenovirus Vectors

High titer adenovirus stocks were prepared from human 293 cells infected with specific adenovirus recombinants. Lysates were subjected to ultracentrifugation through a cesium chloride gradient. Viral bands were extracted and dialyzed against 10 mM Tris (pH 7.5)/135 mM NaCl/5 mM KCl/1 mM $MgCl_2$. Purified viruses were filter sterilized with glycerol added to 10%, and stored in aliquots at −80° C. Titer for adenovirus stocks was determined by plaque assay.

Luciferase Assay

The amount of luciferase in the skin was determined as previously described (Tang, 1994). Briefly, a piece of excised skin was homogenized with a Kontes glass tissue grinder in lysis buffer. After removing tissue debris by centrifugation, luciferase activity in the skin extract was determined with a luminometer by measurement of integrated light emission in the presence of excess ATP and luciferin.

β-Galactosidase Assay

A piece of excised skin was quickly frozen in Tissue-Tek O.C.T. compound (Miles Laboratories Inc.) in liquid nitrogen and stored at −80° C. until use. The frozen tissue was cross sectioned at 4 µm, fixed in 4% paraformaldehyde, and stained for β-galactosidase activity by incubation in X-gal staining solution as previously described (Tang et al., 1994). Sections were counterstained with haematoxylin and eosin.

Preparation of DNA/adenovirus Complexes

DNA/adenovirus complexes were prepared by mixing 100 µg plasmid DNA with $1 \times 10^{11}$ particles of adenovirus in the presence of the condensing agent polylysine for each application. The titer of adenovirus was determined by absorbance.

Preparation of DNA/liposome Complexes

DNA/liposome complexes were prepared by mixing 100 µg plasmid DNA with 100 µg DOTAP/DOPE (1:1; Avanti) for each application. Plasmids were prepared using Qiagen Plasmid Maxi Kits.

Western Blot Analysis

Sera from tail bleeds were diluted 1:250 to 1:500 and reacted with purified proteins that had been separated in a SDS-polyacrylamide gel and transferred to an Inmmobilon-P membrane (Millipore). Reaction was visualized using the ECL kit (Amersham).

Example 1

The present invention demonstrates that antigen genes can be delivered into the skin of mice in a simplified manner by skin-targeted non-invasive delivery of a genetic vector without using sophisticated equipment. FIG. 1 shows that substantial amounts of luciferase enzyme was produced after delivery of limited amounts of AdCMV-luc (an adenovirus vector encoding the firefly luciferase) (Tang et al., 1994) onto the skin. Ad, adenovirus; pfu, plaque-forming units; LU, light units. Results are the mean log[LU per $cm^2$ skin]± SE (n is shown on top of each column). Mice mock-applied or coated with an adenovirus vector that did not encode luciferase produced no detectable luciferase activity in the skin. The level of transgene expression from the adenovirus vector in the skin did not appear to correlate with the titer of the virus. It is possible that only a small number of cells can be transduced by the virus in a restricted subset of skin, and $10^8$ plaque-forming units (pfu) of adenovirus recombinants may have saturated the target cells. This variability could also be due, in part, to variations of individual mice. In addition, some of the variability probably arose from the procedure for removing cornified epithelium which had not been standardized (Johnston and Tang, 1994). The amount of antigen produced may potentially be amplified by applying more vectors onto a larger area.

Example 2

Figure 2B:
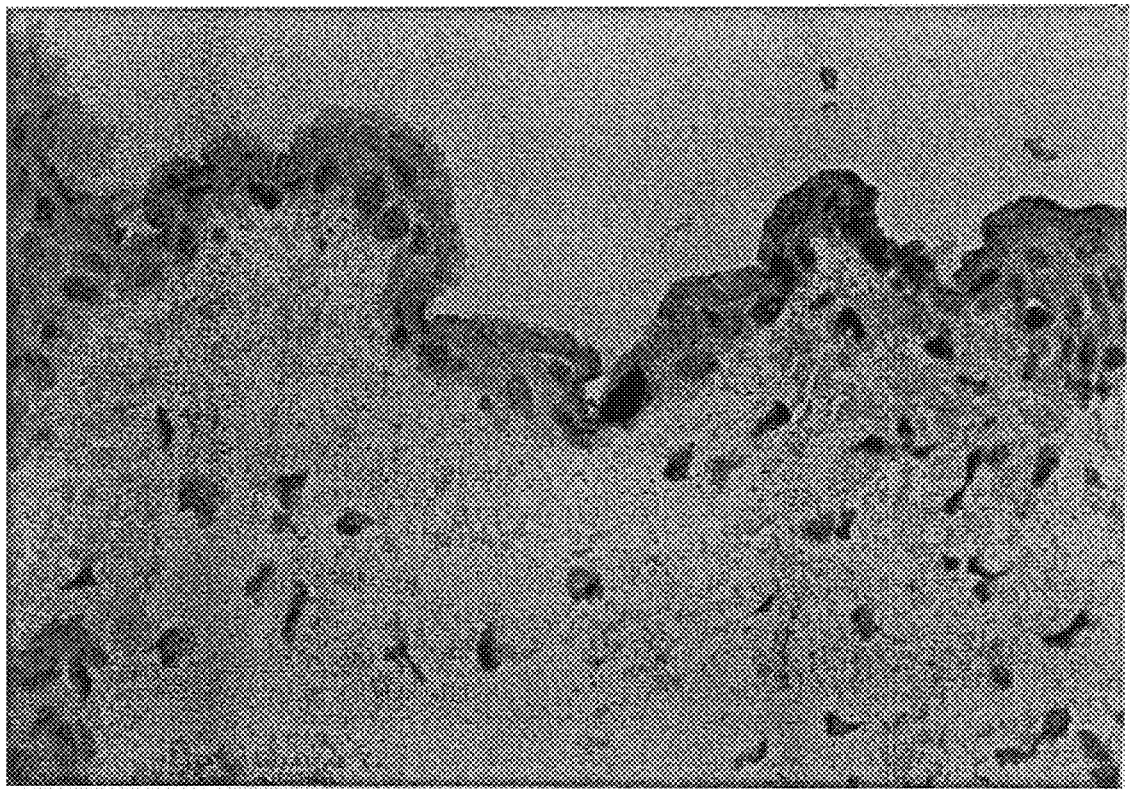

The principal target cells for non-invasive vaccination onto the skin appeared to be hair matrix cells within hair follicles (FIG. 2a) and keratinocytes within the outermost layer of epidermis (FIG. 2b) as shown by staining frozen sections with X-gal substrates after skin-targeted non-invasive delivery of an adenovirus vector encoding the E. coli β-galactosidase gene (AdCMV-βgal) (Tang et al., 1994). No physical abrasions were found in the skin tissue subjected to the treatment, and there was no inflammation induced. The skin tissue subjected to non-invasive gene delivery was excised from animals 1 day after pipetting $10^8$ pfu of AdCMV-βgal onto the skin, cross sectioned, fixed, and stained with X-gal substrates as described (Tang et al., 1994). FIG. 2a shows the adenovirus-transduced hair matrix cells within a hair follicle, ×150. FIG. 2b shows the adenovirus-transduced keratinocytes within the outermost layer of epidermis, ×150. No blue cells were found in control animals that were either mock-applied or coated with AdCMV-luc.

Example 3

Elicitation of Humoral Immune Responses by Adenovirus-mediated NIVS

Figure 3A:
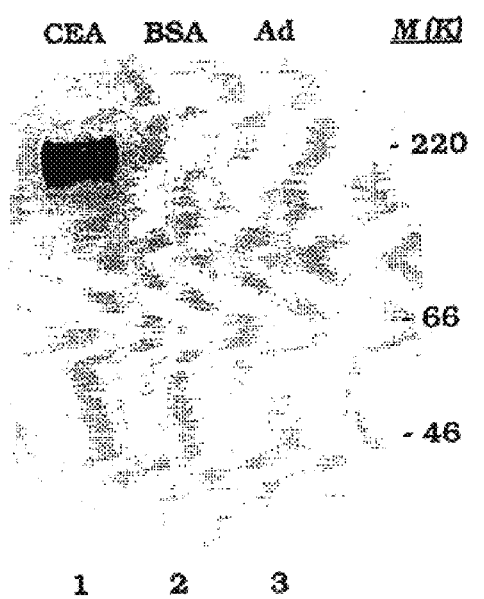
FIGS. 3a and 3b show the detection of specific antibodies in the sera of mice immunized by adenovirus-mediated NIVS.

NIVS is a novel method for vaccinating animals. To demonstrate that the procedure can elicit a specific immune response against the antigen encoded by the vector, AdCMV-hcea (an adenovirus vector encoding the human carcinoembryonic antigen (CEA)) was pipetted onto the skin of the C57BL/6 strain mice. Serum from a vaccinated mouse a month after skin-targeted non-invasive delivery of $10^8$ pfu AdCMV-hcea was diluted 1:500 and reacted with purified human CEA protein (provided by T. Strong) and adenoviral proteins that had been separated in a 5% SDS-polyacrylamide gel, and transferred to Imnmobilon-P membranes (Millipore). Referring to FIG. 3a, lane 1, 0.5 µg of human CEA; lane 2, 0.5 µg of BSA; lane 3, $10^7$ pfu of adenovirus. FIG. 3a shows that the test sera from a vaccinated animal reacted in western blots with purified human CEA protein, but not with bovine serum albumin (BSA), which supports the conclusion that specific antibodies have been produced against exogenous proteins encoded by adenovirus vectors as a result of skin-targeted non-invasive gene delivery.

Figure 3B:
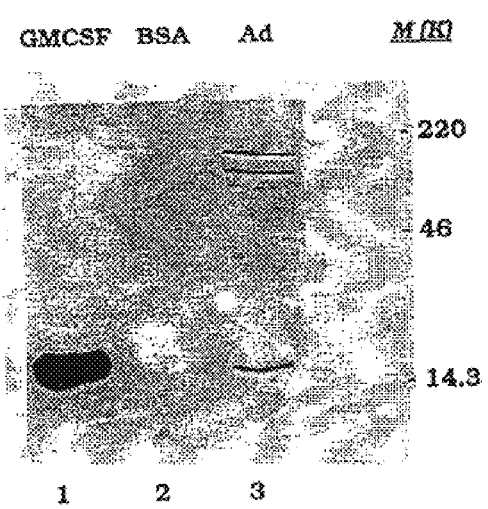

To test whether this technique might be generally applicable, AdCMV-hgmcsf (an adenovirus vector encoding the human granulocyte macrophage colony stimulating factor (hGM-CSF)) was applied onto the skin. To detect antibodies against the human GM-CSF protein, the animal was vaccinated by skin-targeted non-invasive delivery of $10^8$ pfu of AdCMV-hgmesf. Purified human GM-CSF protein (CalBiochem) separated in a 15% SDS-polyacrylamide gel was transferred to membranes and allowed to react with diluted serum. Other treatments were carried out as described in FIG. 3a. Referring to FIG. 3b, lane 1, 0.25 µg of human GM-CSF; lane 2, 0.25 µg of BSA; lane 3, $10^7$ pfu of adenovirus. The replication-defective human adenovirus serotype 5 derived AdCMV-hcea and AdCMV-hgmcsf were produced in human 293 cells. A cassette containing the human CEA gene or the human GM-CSF gene, driven by the cytomegalovirus (CMV) early enhancer-promoter element was inserted in place of the E1a deletion. Since the sequences in the E1a region were deleted, the ability of these viruses to replicate autonomously in nonpermissive cells was impaired.

Results (Tang et al., 1997) show that 96% (23/24) of the C57BL/6 strain mice produced antibodies against the human CEA protein a month after skin-targeted non-invasive delivery of AdCMV-heea, and 43% (6/14) of the same strain mice produced antibodies against the human GM-CSF protein after skin-targeted non-invasive delivery of AdCMV-hgmcsf. Both pre-immune sera collected before NIVS and sera from naive animals failed to react with the human CEA and GM-CSF proteins. The possibility of oral vaccination by ingesting vectors through grooming was eliminated by (1) rinsing vectors away from the skin before animals recovered from anesthesia, (2) pipetting vectors onto unshaved skin, and (3) mixing naive and vaccinated animals in the same cage. No cross-vaccination between naive and vaccinated mice was ever observed, and shaving appeared as an essential component for NIVS presumably due to the mechanical removal of cornified epithelium along the shaving path. Thus, adenovirus-mediated NIVS is capable of eliciting a humoral immune response against an antigen encoded by the vector.

Example 4

Figure 4:
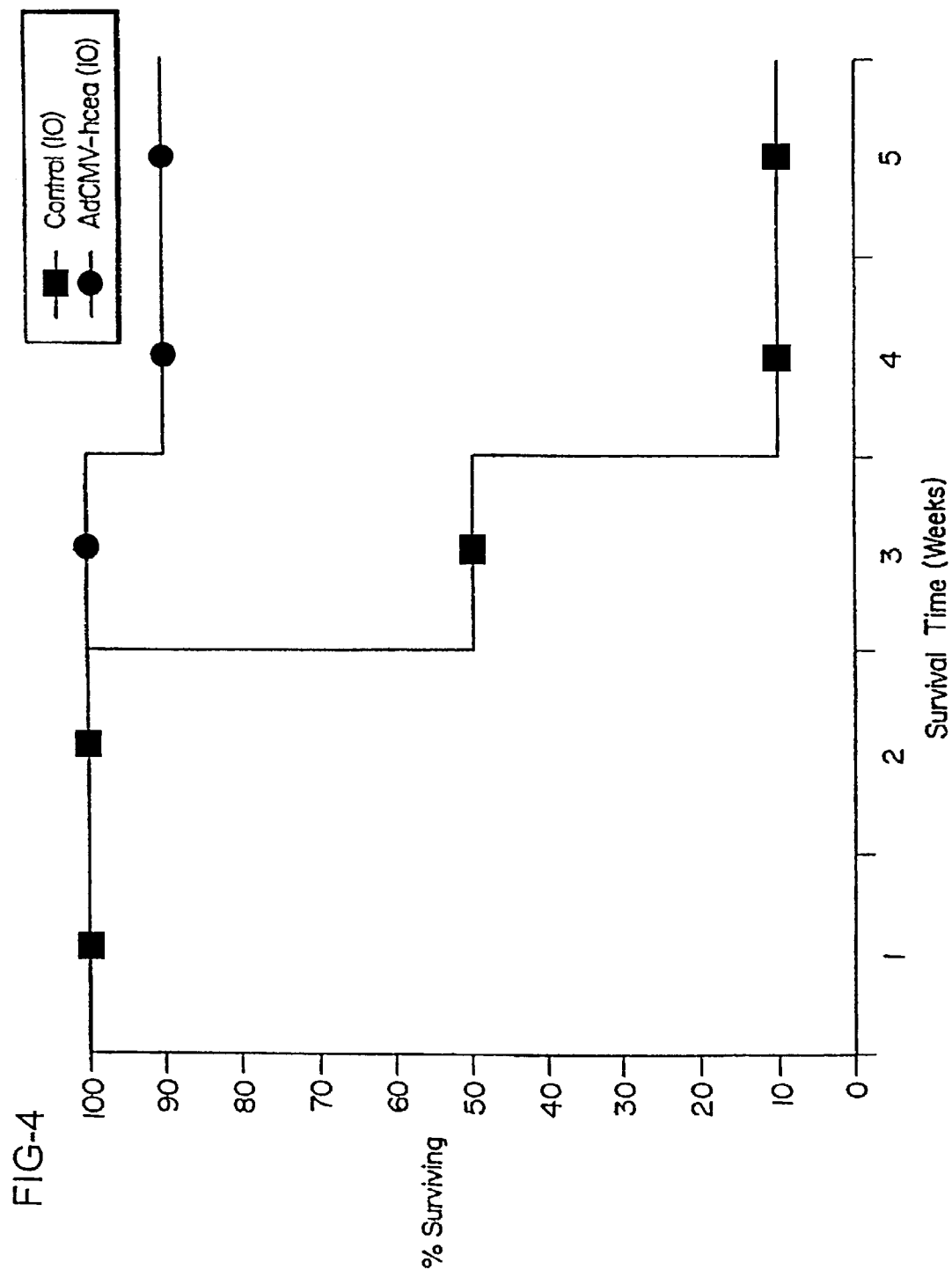
FIG. 4 shows the percent survival of control versus immunized mice that were challenged by a lethal dose of tumor cells.

To demonstrate that the techniques of the present invention can elicit a protective antitumor immune response, syngeneic tumor cells that express the human carcinoembryonic antigen (CEA) gene (MC38-CEA-2) (Conry et al., 1995) were inoculated into naive C57BL/6 strain mice and the same strain mice that had been vaccinated by topical application of an adenovirus vector encoding the human CEA gene (AdCMV-hcea). Animals subjected to tumor challenges were observed for survival (FIG. 4). In the control group, 90% (9/10) of the animals developed palpable tumor nodules and died within 30 days after tumor cell implantation. In the vaccinated group, only 10% (1/10) of the animals died, and 70% (7/10) of them remained totally tumor-free. Mice were euthanized when the tumor exceeded 1 cm in diameter. The interval between tumor cell injection and euthanization is used as the individual survival time. Referring to FIG. 4, control mice (no vaccines were administered) and animals immunized by NIVS ($10^8$ pfu of AdCMV-hcea were topically applied a month before) were subjected to tumor challenges. Numbers in parentheses represent the number of animals for each treatment. Results show that non-invasive delivery of genetic vaccines onto the skin may be able to elicit protective immune responses against tumor cells expressing a specific antigen.

Example 5

Construction of Recombinant Adenovirus Vectors Encoding Catokine and Co-stimulatory Genes Adenovirus vectors encoding co-stimulatory and cytokine genes were constructed for the co-delivery of these immune-modulatory genes with antigen genes into skin cells in an attempt to direct the immune profile in vaccinated animals. The adenovirus vector AdCMV-mB7.1 encoding the murine B7-1 gene and the adenovirus vector AdCMV-mgmcsf encoding the murine GM-CSF gene were constructed by homologous recombination between two transfected plasmids in human 293 cells following a standard procedure for generating new adenovirus vectors (Gomez-Foix et al., 1992). All transgenes in these vectors were transcriptionally driven by the CMV early enhancer-promoter element. AdCMV-mB7.1 was characterized by staining transduced human lung carcinoma SCC-5 cells with the anti-CD80 antibody (PharMingen), followed by flow cytometric analysis. AdCMV-mgmcsf was characterized by measuring murine GM-CSF secreted from transduced SCC-5 cells with an ELISA kit (Amersham).

Example 6

Detection of Antitumor Immunity by In Vivo Cytotoxicity Assay

An in vivo cytotoxicity assay was developed in which target cells were implanted as monolayers onto the muscle tissue of mice (Tang et al., 1996). Implantation of target cells as monolayers allowed for an efficient retrieval of target cells for assessing their fates after a few days of in vivo growth. This assay was particularly useful for detecting weak immune responses that are not potent enough for eradicating target cells. Immune responses can be characterized by histological analysis of the implantation bed. Without an immune response, target cells would grow. With a potent immune response, target cells would be eradicated in the presence of a large number of immune effector cells at the implantation bed, probably by virtue of migration to and in situ sensitization around growing target cells. With a weak immune response, growing target cells would intermingle with infiltrating immune effector cells at the implantation bed. Implanting $5 \times 10^5$ RM1-luc cells (RM1 prostate tumor cells expressing the luciferase gene) as a monolayer into naïve C57BL/6 mice resulted in a tumor layer due to proliferation of RM1-luc cells in vivo, with no evidence of immune intervention. In contrast to control animals, RM1-luc cells were intermingled with a large number of immune effector cells at the implantation bed in animals vaccinated by skin-targeted non-invasive delivery of AdCMV-luc.

Example 7

Characterization of Immune Effector Cells Recruited by Tumor Cells

The in vivo cytotoxicity assay was able to concentrate a large number of immune effector cells at the implantation bed by implanting a small number of target cells as a monolayer onto muscle. Characterization of specific immune effector cells at the implantation bed may provide evidence as to whether a cell-mediated immune response has been elicited for killing target cells. For characterizing T cells that were recruited by luciferase-expressing tumor cells in animals vaccinated by skin-targeted non-invasive delivery of AdCMV-luc, tissue sections of the implantation bed were stained with an anti-CD3 monoclonal antibody (mAb). RM1-luc cells were produced by lipofecting pHBA-luc DNA into RM1 prostate tumor cells (provided by T. Thompson at the Baylor College of Medicine), followed by selection in medium containing G418. Clones expressing luciferase were characterized by luciferase assay. Five $\times 10^5$ RM1-luc cells were implanted as a monolayer into a mouse that had been vaccinated by skin-targeted non-invasive delivery of $10^8$ pfu AdCMV-luc. Five days after implantation, the implantation bed was frozen in O.C.T. and sections were cut at 4 μm, dried in 100% acetone, and stained with an anti-CD3 mab (clone F500A2, provided by P. Bucy at UAB), via the ABC immunoperoxidase procedure with diaminobenzidine as the chromogen.

Figure 5:
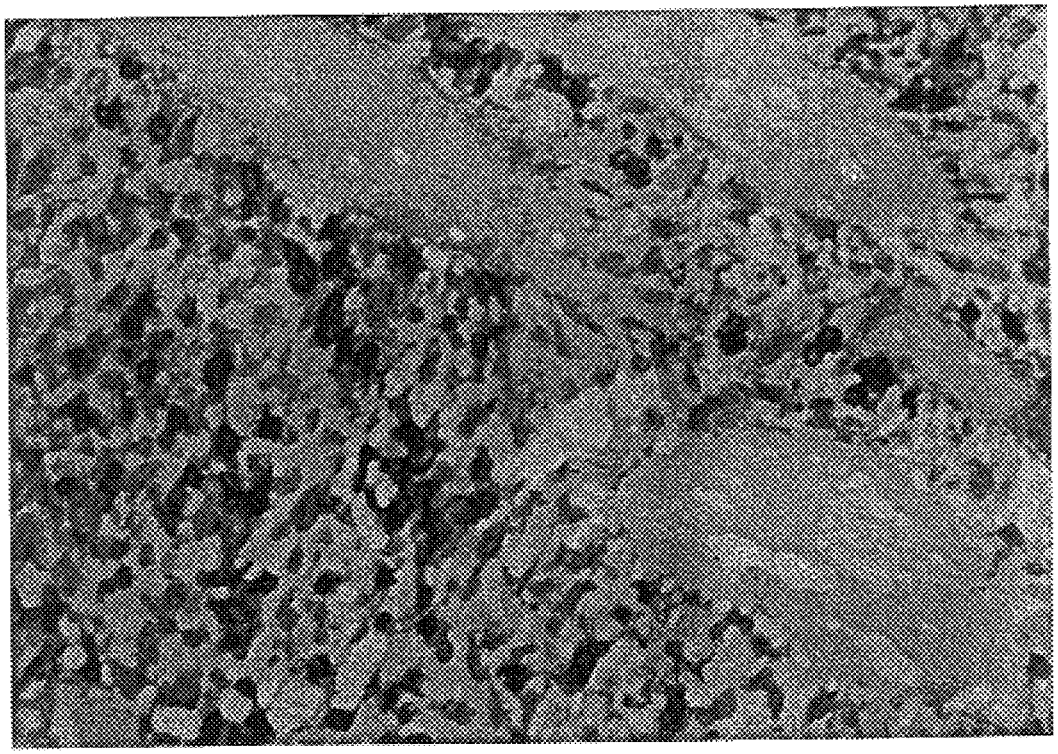
FIG. 5 shows the characterization of tumor-infiltrating T lymphocytes.

As shown in FIG. 5, a large number of T cells infiltrated into the implantation bed after 5 days of in vivo growth of RM1-luc cells in a mouse vaccinated by skin-targeted non-invasive delivery of AdCMV-luc (×50) while only a few T cells were found in naïve animals. It appeared that the same number of RM1-luc target cells could recruit more T lymphocytes to the implantation bed in vaccinated animals than in naive animals.

For characterizing CTLs that were recruited by target cells, frozen sections of the implantation bed were subjected to in situ hybridization using an antisense granzyme A RNA molecule as the probe. Five ×10$^5$ RM1-luc cells were implanted as a monolayer into either a naive C57BL/6 mouse or a mouse that had been vaccinated by skin-targeted non-invasive delivery of 10$^8$ pfu AdCMV-luc. Five days after implantation, the implantation bed was frozen in O.C.T. and sections were cut at 4 $\mu$m. Frozen sections were fixed in 3% paraformaldehyde, incubated in 0.2 M HCl for inhibiting endogenous alkaline phosphatase activity, and hybridized with a heat-denatured antisense granzyme A RNA probe. Probes for in situ hybridization were single-stranded RNA molecules produced by transcription from a plasmid containing bacteriophage promoters. During the transcription, digoxigenin-UTP was directly incorporated into the sequence. Sense sequence probes were used as negative controls. After hybridizing with probes, sections were washed and incubated with alkaline phosphatase-conjugated anti-digoxigenin antibody, followed by incubation in the NBT/BCIP enzyme substrate solution.

Figure 6:
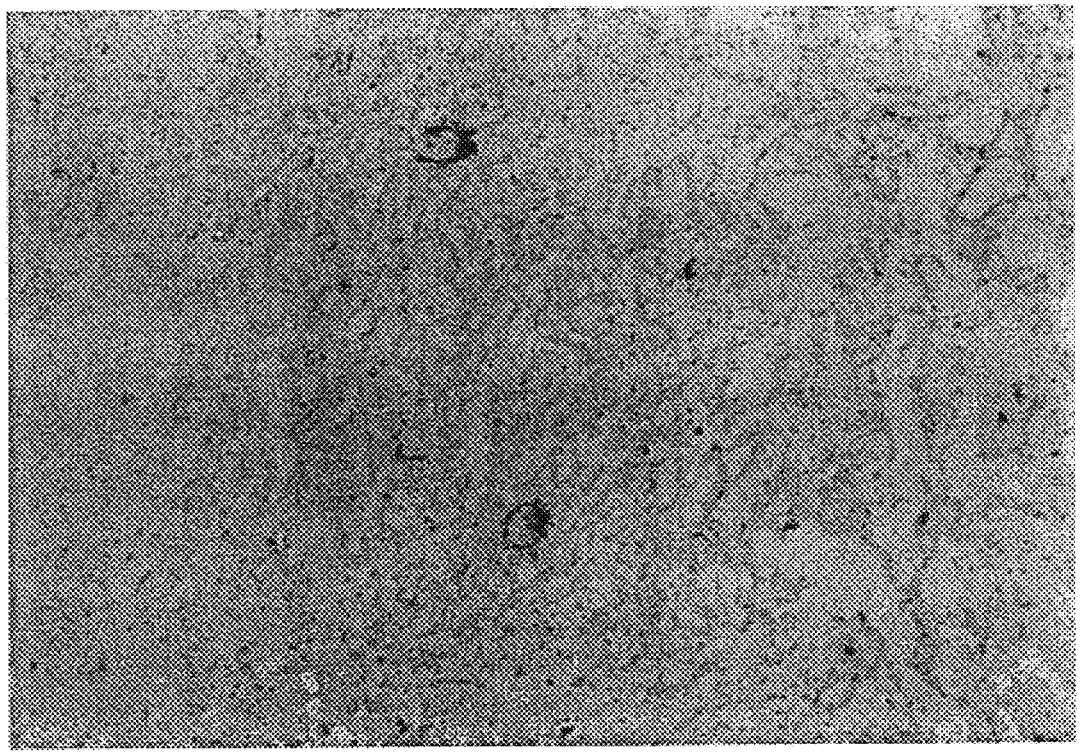
FIG. 6 shows the characterization of tumor-infiltrating CTLs.

CTLs that express granzyme A are activated CTLs and have been used as predictive markers for tissue rejection during transplantation. Granzyme-positive CTLs were found within the RM1-luc implantation bed only in animals that had been vaccinated by skin-targeted non-invasive delivery of AdCMV-luc (FIG. 6). Their presence at the bed suggests that a cell-mediated immune response against tumor cells expressing a specific antigen may have been induced by NIVS.

Example 8

Topical Application of Genetic Vaccines by Adhesive Bandages

It was demonstrated, for the first time, that bandages could be used for the administration of vaccines. This development may allow personnel without medical training to deliver a uniform dose of non-invasive vaccines onto the skin. To transduce skin by bandage, 50 $\mu$l of the AdCMV-luc vector described in Example 7 was pipetted into the pad of an adhesive bandage (Johnson & Johnson). The vector-containing bandage was subsequently adhered to pre-shaved skin of a mouse. The vector was kept in contact with naked skin for 18 hours. To detect transgene expression from genetic vectors delivered by a bandage, the skin was assayed for luciferase (Table 1). While the results show substantial variation, transgene expression in the skin was achievable using adhesive bandages.

Figure 7:
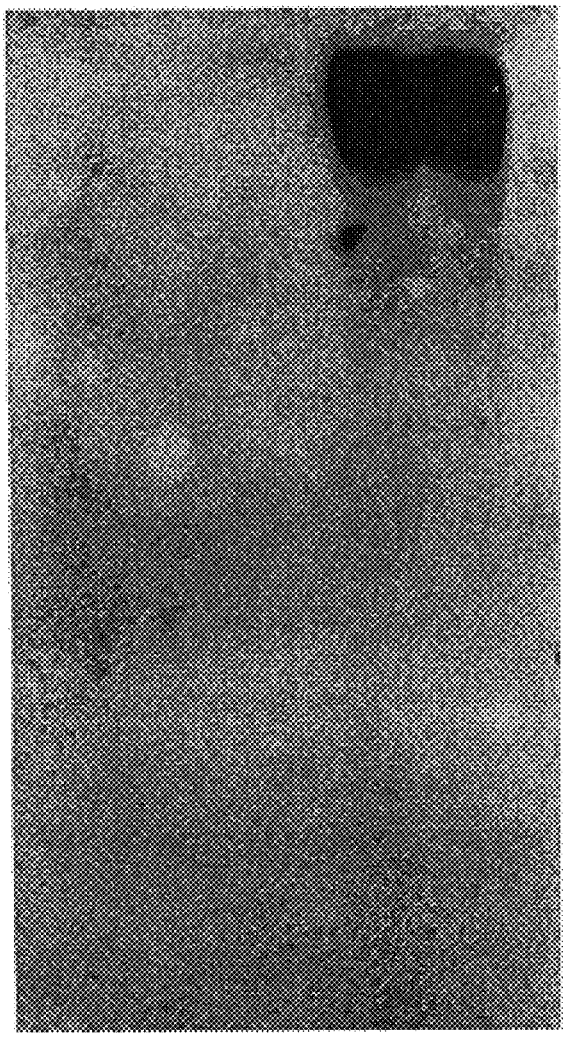
FIG. 7 shows the western blot analysis of antibodies to the human CEA protein in mice immunized by topical application of vaccine bandages.

To demonstrate that animals could be vaccinated with non-invasive adhesive bandages, sera from tail bleeds were assayed for anti-CEA antibodies two months after adhering bandages containing AdCMV-hcea onto the skin of mice. As shown in FIG. 7, anti-CEA antibodies were detected in 100% (10/10) of mice that received non-invasive vaccines through adhesive bandages.

Example 9

DNA/adenovirus-mediated NIVS

Adenovirus-based vectors can be made more versatile by binding plasmid DNA to the exterior of an adenovirus. The resulting vector system mediates high-efficiency gene delivery to a wide variety of target cells. This approach allows greatly. enhanced flexibility in terms of the size and design of foreign genes. DNA/adenovirus complexes may thus be able to deliver antigen genes into the skin via the same adenovirus receptor-mediated endocytosis pathway with more flexibility.

Figure 8A:
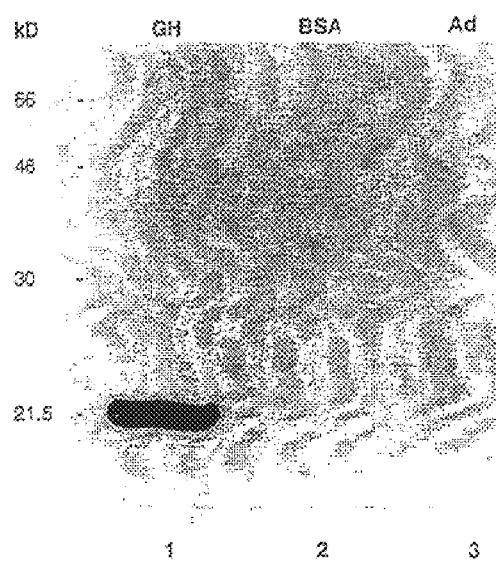
FIG. 8a shows the detection of specific antibodies in the serum of a mouse immunized by DNA/adenovirus-mediated NIVS.
Figure 8B:
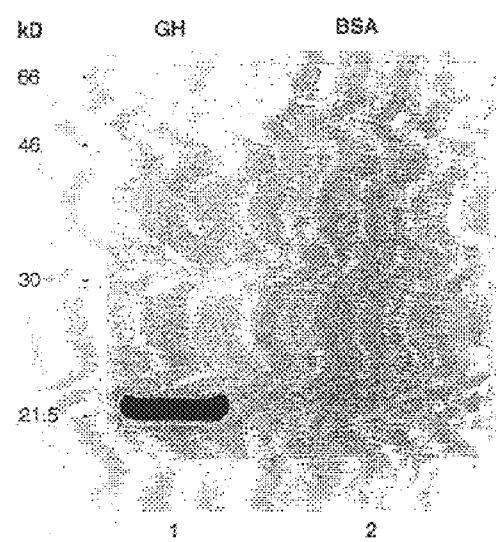
FIG. 8b shows the detection of specific antibodies in the serum of a mouse immunized by DNA/liposome-mediated NIVS.

To demonstrate the feasibility of DNA/adenovirus-mediated NIVS, plasmid DNA encoding the human growth hormone (pCMV-GH) (Tang et al., 1992) was allowed to complex with an E4-defective adenovirus. Mice (strain C57BL/6) were vaccinated by contacting DNA/adenovirus complexes with naked skin for one day. Immunized animals were subsequently monitored for the production of antibodies against the human growth hormone protein (hGH) by assaying sera from tail-bleeds. As shown in FIG. 8$a$, lane 1, hGH (0.5 $\mu$g); lane 2, BSA (0.5 $\mu$g), the test sera reacted in western blots with purified hGH, but not with irrelevant proteins. Of ten mice vaccinated by DNA/adenovirus complexes, eight (80%) produced antibodies against hGH within three months, indicating that specific antibodies could be produced against exogenous proteins encoded by plasmid DNA that is complexed with adenovirus and administered in a non-invasive mode. Pre-immune sera collected before treatment, sera from untreated animals, and sera from animals vaccinated with irrelevant vectors all failed to react with hGH. Thus, DNA/adenovirus complexes, like adenovirus recombinants, appear as a legitimate vector system for NIVS.

Example 10

DNA/liposome-mediated NIVS

In addition to developing genetic vectors involving adenovirus as carriers for non-invasive vaccines, it has also been demonstrated that mice could be vaccinated by topical application of DNA/liposome complexes without viral elements. It is apparent that many different vectors can be applied in a creative way for the administration of skin-targeted non-invasive vaccines. As shown in FIG. 8$b$, lane 1, hGH (0.5 $\mu$g); lane 2, BSA (0.5 $\mu$g), the test serum from a mouse immunized by topical application of DNA/liposome complexes encoding hGH reacted with hGH but not with BSA. Of 10 mice vaccinated by DNA/liposome complexes, the test sera reacted with purified hGH in 9 (90%) treated animals within 5 months. Thus, the DNA/liposome complex, like the adenovirus and the DNA/adenovirus complex, appears as another legitimate vector system for NIVS.

Example 11

Co-expression of DNA-encoded and Adenovirus-encoded Transgenes

Strategies of augmenting the immune system's response can potentially improve the clinical outcomes of vaccines. Local production of immune-modulatory molecules involved in the activation and expansion of lymphocyte populations may significantly improve the vaccination effects. Adenovirus vectors encoding the murine B7-1 and GM-CSF genes have been made. Topical application of DNA/adenovirus complexes may thus be able to co-express DNA-encoded antigens or immune modulatory molecules with adenovirus-encoded antigens or immune modulatory molecules in individual skin cells for enhancing the immune response against the antigen.

Figure 9:
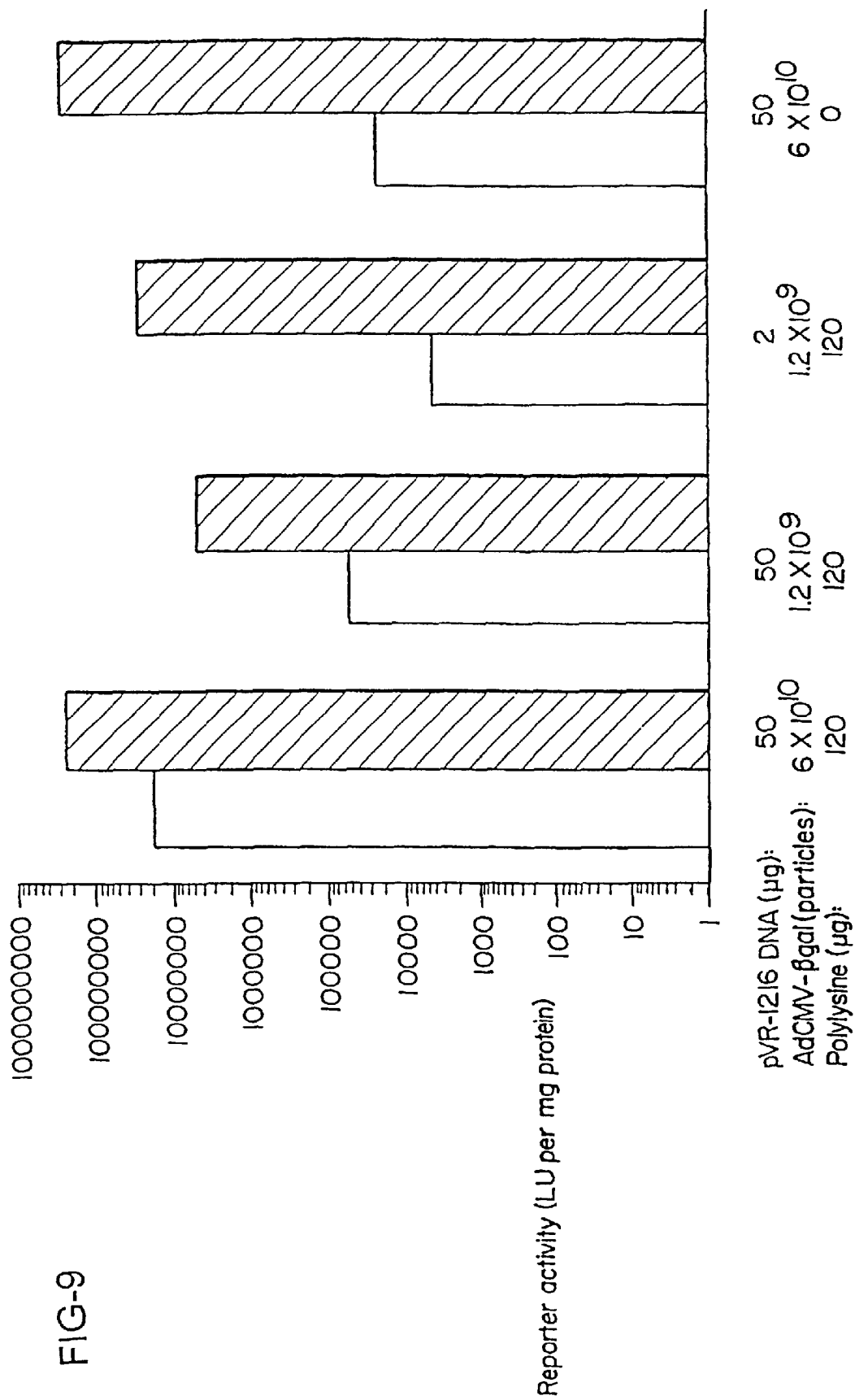
FIG. 9 shows the co-expression of DNA-encoded and adenovirus-encoded transgenes in target cells.

FIG. 9 shows that the expression of transgenes from plasmid DNA in target cells is dependent upon the presence of adenovirus, thus allowing plasmid-encoded and adenovirus-encoded transgenes to be co-expressed in the same cell. pVR-1216 plasmid DNA (provided by Vical), AdCMV-βgal particles and polylysine were mixed at specific ratios as shown in the figure. The complex was applied to $2 \times 10^5$ SCC-5 cells in a well and incubated for 2 hours. The complex was then removed and cells were harvested for luciferase and β-galactosidase assays the next day. Open column: luciferase activity; solid column: β-galactosidase activity. Results show that DNA-encoded transgenes are not expressed in target cells in the absence of adenovirus, whereas adenovirus-encoded transgenes can be expressed in the presence of DNA. It is also possible that DNA may be condensed onto the surface of other viruses for targeting different cell types. Accordingly, this protocol provides a simple but versatile gene delivery system which allows the expression of transgenes from both a virus recombinant and an externally-bound plasmid, simultaneously.

Example 12

Figure 10:
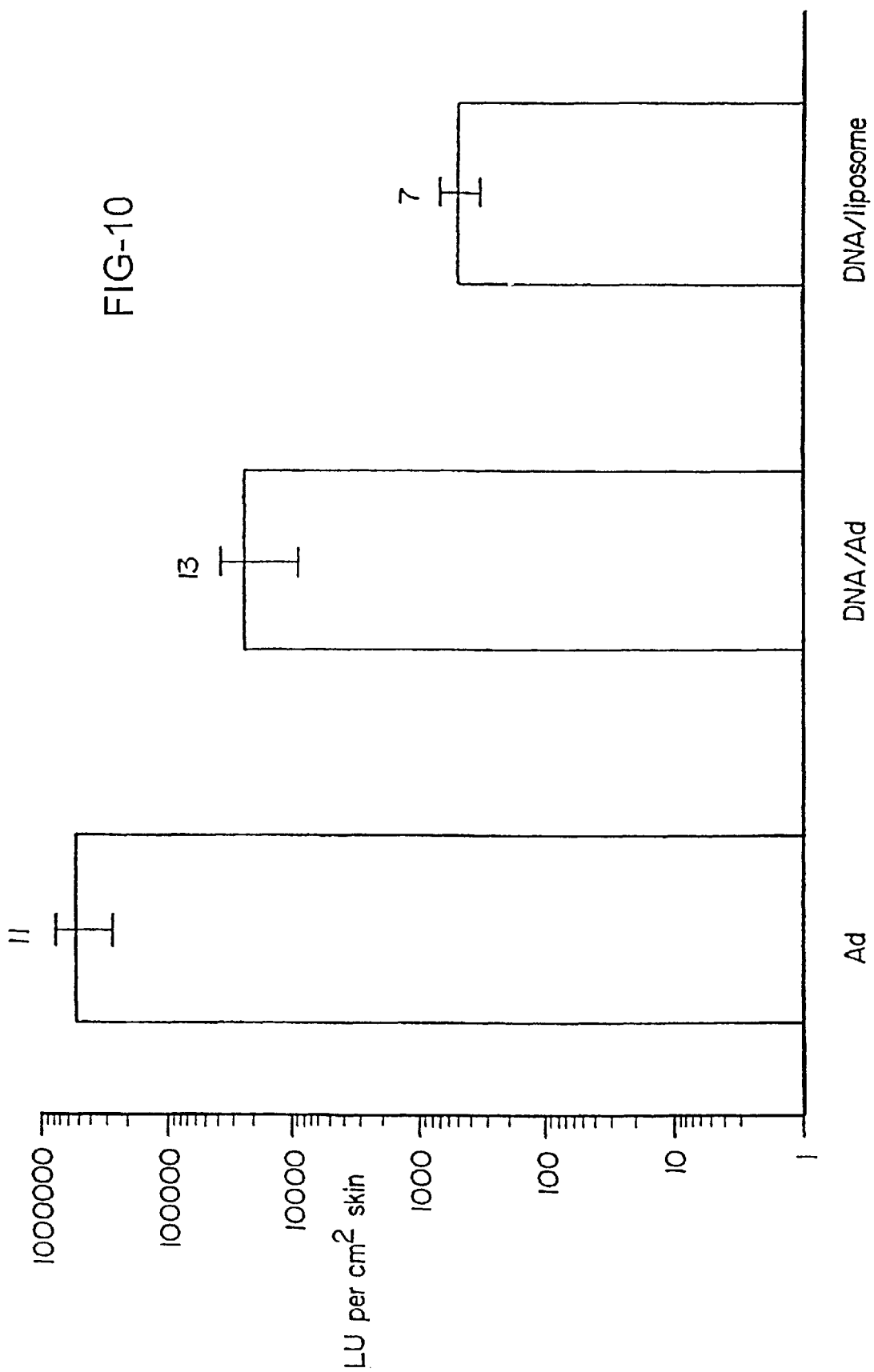
FIG. 10 shows relative transgene expression from topically-applied adenovirus recombinants, DNA/adenovirus complexes, and DNA/liposome complexes.

Relative Transgene Expression in the Skin from Different Genetic Vectors by Topical Application It has been shown that adenovirus recombinants, DNA/adenovirus complexes, DNA/liposome complexes, and perhaps many other genetic vectors can all be applied as carriers for non-invasive vaccines. It is conceivable that the higher the efficiency for transgene expression, the more powerful the carrier will be. To define the relative efficiencies for the vectors utilized, adenovirus recombinants, DNA/adenovirus complexes, or DNA/liposome complexes were allowed to contact mouse skin by topical application for 18 hr. The treated skin was subsequently removed from the animal and assayed for luciferase activity with a luminometer by measurement of integrated light emission for 2 min using the Promega's luciferase assay system, and background was subtracted from the readings. As shown in FIG. 10, adenovirus recombinants were found to be the most efficient vector system for skin-targeted non-invasive gene delivery. Mice mock-treated produced no detectable luciferase activity in the skin. LU, light units; Ad, AdCMV-luc; DNA/Ad, pVR-1216 DNA complexed with Ad dl1014; DNA/liposome, pVR-1216 DNA complexed with DOTAP/DOPE. Results are the mean log(LU per $cm^2$ skin)±SE (n is shown on top of each column). Although the efficiency of DNA/adenovirus complex is lower than that of adenovirus recombinant, it is significantly higher than that of DNA/liposome complex. In addition, adenovirus may be inactivated by UV or gamma irradiation before complexing with DNA to prevent viable viral particles from disseminating. Thus, DNA/adenovirus complexes may appear as the most promising carrier system for the delivery of non-invasive vaccines when efficiency and safety factors are both considered in formulating a new generation of vaccines.

Example 13

Construction of an Expression Vectors Encoding Influenza Antigens

An E1/E3-defective adenovirus recombinant encoding the AIPR/8/34 HA gene (AdCMV-PR8.ha) was constructed as described (Gomez-Foix et al., 1992). Briefly, an 1.8 kb BamHl fragment containing the entire coding sequence for HA was excised from the plasmid pDP122B [American Type Culture Collection (ATCC)] and subsequently inserted into the BamHl site of pACCMV.PLPA in the correct orientation under transcriptional control of the human cytomegalovirus (CMV) early promoter. The resulting plasmid encoding HA was co-transfected with the plasmid pJM17 into human 293 cells for generating E1/E3-defective adenovirus recombinants. An E1/E3-defective adenovirus recombinant encoding the A/PR/8/34 nuclear protein (NP) gene (AdCMV-PR8.np) was constructed by cloning the NP gene (provided by Merck) into pACCMV.PLPA, followed by homologous recombination in 293 cells as described above.

A plasmid expression vector encoding HA (pCMV-PR8.ha) and another encoding NP (pCMV-PR8.np) were constructed by cloning the HA and NP genes into pVR1012 (provided by Vical), respectively.

Example 14

Figure 12:
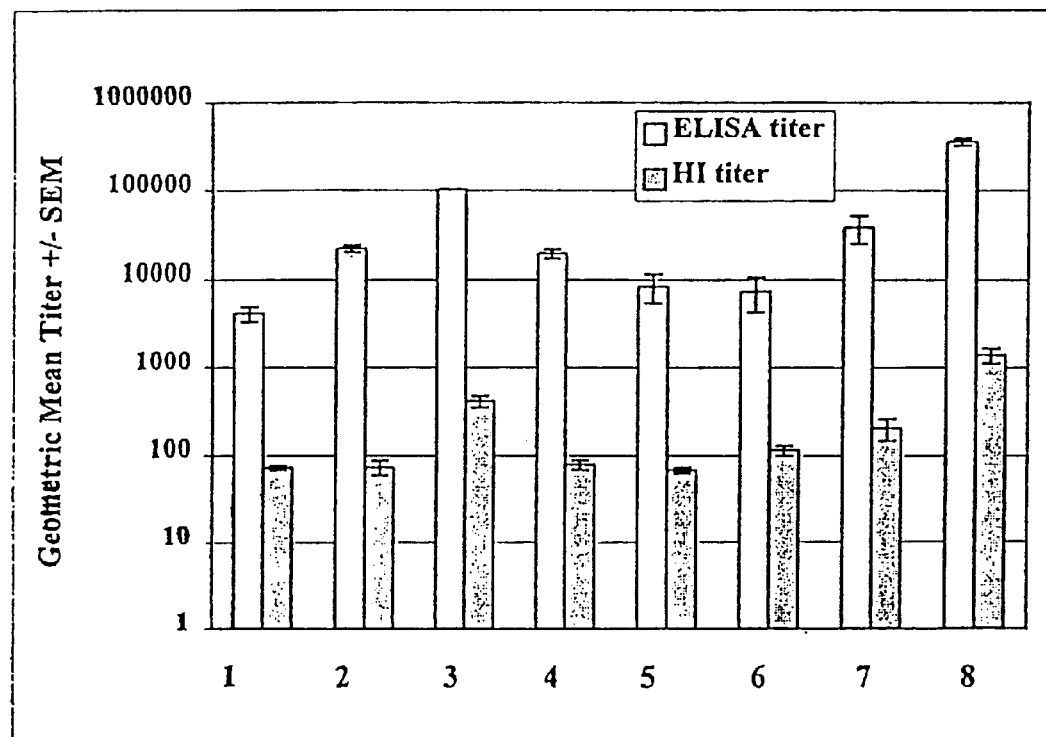
FIG. 12 shows anti-influenza antibodies generated by skin-targeted noninvasive vaccines in mice.

Anti-influenza Antibodies Generated by Topical Application and Intranasal Inoculation of Adenovirus Based Vaccines in Mice As shown in FIG. 12, BALB/c mice (3 months old) were immunized by a variety of vaccination modalities including intramuscular injection of DNA, intranasal inoculation of adenovirus vectors, and topical application of an adenovirus-based vaccine patch. Skin-targeted non-invasive vaccination was carried out by pipetting adenovirus vectors onto pre-shaved abdominal skin followed by covering the vector as a thin film over naked skin with a piece of the Tegaderm patch (3M). Unabsorbed vectors were washed away in an hour. All animals were immunized 3 times every 3 weeks. Serum samples were assayed for anti-influenza antibodies 1 week after the last boost. Titers of anti-influenza IgG were determined by ELISA as described (12) using purified A/PR/8/34 virus as the capture antigen. Serun samples and peroxidase-conjugated goat anti-mouse IgG (Promega) were incubated sequentially on the plates for 1 hour at room temperature with extensive washing between each incubation. The end-point was calculated as the dilution of serum producing the same $OD_{490}$ as a 1/100 dilution of preimmune serum. Sera negative at the lowest dilution tested were assigned endpoint titers of 100. The postimmune sera also reacted with a control antigen (e.g., BSA) at a low level. Hemagglutination inhibition (HI) assay was carried out for measuring the ability of anti-HA antibodies to inhibit the agglutination of red blood cells (RBC) by virus, possibly by blocking cell surface binding. Serum samples preabsorbed with chicken RBCs were diluted and mixed with 4 HA units of influenza A/PR/8/34. Chicken RBCs were then added to a final concentration of 0.5%. Agglutination was determined by visual examination. The titer was defined as the dilution being the limit of inhibition. All preimmune sera had titers of $\leq 20$. Group 1, intranasal inoculation of $2.5 \times 10^7$ pfu wild-type adenovirus serotype 5 followed by topical application of $10^8$ pfu AdCMV-PR8.ha and $10^8$ pfu AdCMV-PR8.np 2 weeks later (n=9); Group 2, intranasal inoculation of $2.5 \times 10^7$ pfu wild-type adenovirus serotype 5 followed by intramuscular injection of 100 μg pCMV-PR8.ha DNA and 100 μg pCMV-PR8.np DNA 2 weeks later (n=10); Group 3, intranasal inoculation of $2.5 \times 10^7$ pfu wild-type adenovirus serotype 5 followed by intranasal inoculation of $2.5 \times 10^7$ pfu AdCMV-PR8.ha and $2.5 \times 10^7$ pfu AdCMV-PR8.np 2 weeks later (n=8); Group 4, topical application of $10^8$ pfu AdCMV-PR8.ha and $10^8$ pfu AdCMV-PR8.np (n=10); Group 5, topical application of $10^8$ pfu AdCMV-PR8.np (n=10); Group 6, topical application of $10^8$ pfu AdCMV-PR8.ha (n=10); Group 7, intramuscular injection of 100 μg pCMV-PR8.ha DNA and 100 μg pCMV-PR8.np DNA (n=10); Group 8, intranasal inoculation of 2.5×10⁷ pfu AdCMV-PR8.ha and 2.5×10⁷ pfu AdCMV-PR8.np (n=9). The data was plotted as geometric mean endpoint titers. In the naïve control group (n=7), no anti-influenza antibodies were detectable. The analysis of variance (ANOVA) approach was utilized to compare the differences in ELISA and HI titers. Multiple pairwise comparisons were made with Tukey's procedure with the overall alpha level set at 0.05. The analyses were performed in log scale of the measurements to meet the constant variance assumption required by the ANOVA approach. The differences in ELISA and HI titers among the 8 groups were significant (P<0.0001). The ELISA titer in group 8 was significantly higher than that in other groups (P<0.02). The average ELISA titer in group 1 was the lowest but was not significantly different from that in group 5 or 6. The HI titer in group 8 was the highest and that in group 3 was the second highest. The HI titer values in groups 1, 2, 4, 5, and 6 were not significantly different.

Example 15

Protection of Mice from Death Following Virus Challenge

Figure 13:
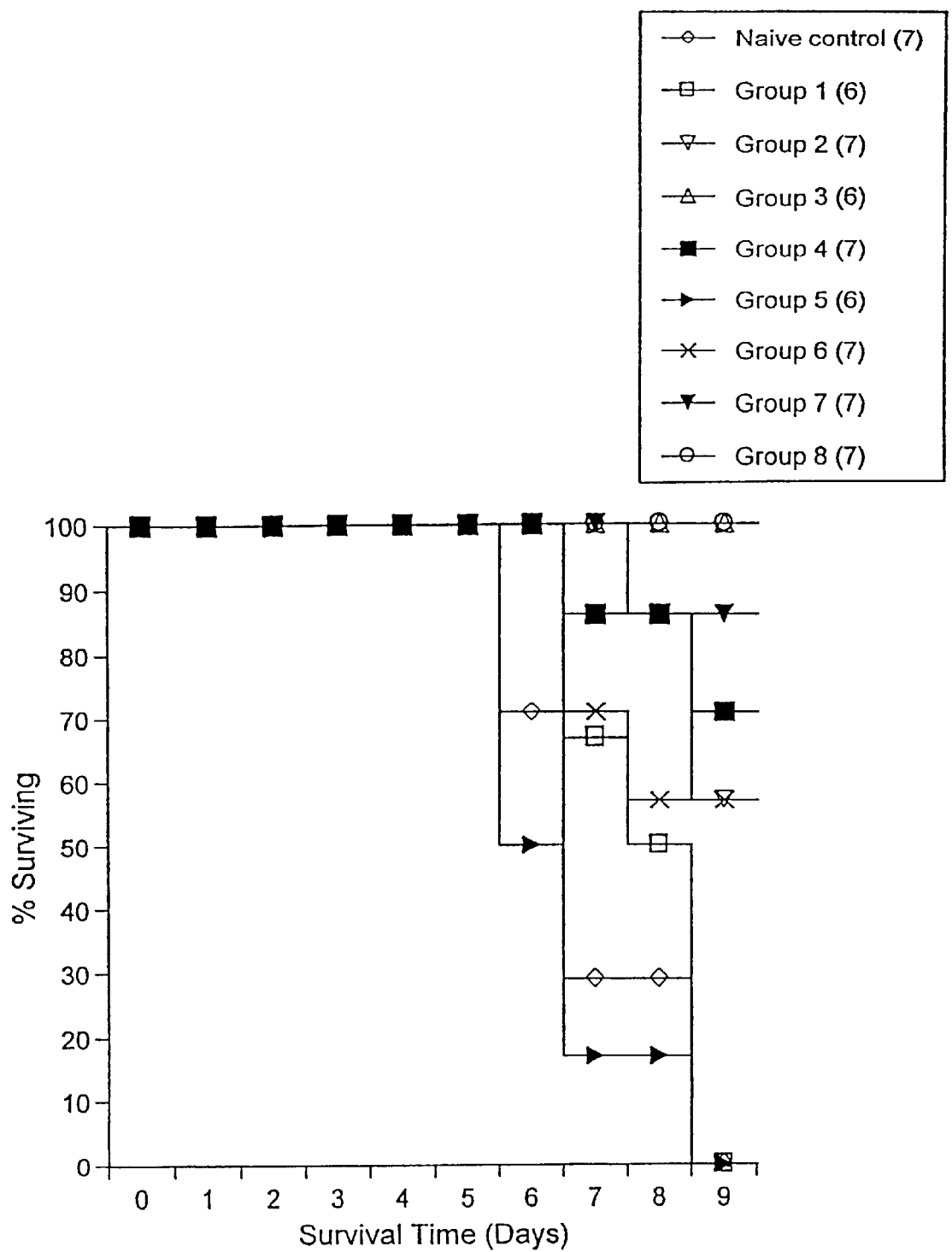
FIG. 13 shows protection of mice from death following virus challenge.

As shown in FIG. 13, BALB/c mice (3 months old) were immunized by a variety of vaccination modalities including intramuscular injection of DNA, intranasal inoculation of adenovirus vectors, and topical application of an adenovirus-based vaccine patch. Skin-targeted noninvasive vaccination was carried out by pipetting adenovirus vectors onto pre-shaved abdominal skin followed by covering the vector as a thin film over naked skin with a piece of the Tegaderm patch (3M). Unabsorbed vectors were washed away in an hour. All animals were immunized 3 times every 3 weeks. One week after the last boost, mice were challenged intranasally with a lethal dose of influenza virus A/PR/8/34 (1,000 HA units) and monitored daily for survival. The data was plotted as % survival versus days after challenge. Naïve Control, naïve mice without exposure to adenovirus; Group 1, intranasal inoculation of 2.5×10⁷ pfu wild-type adenovirus serotype 5 followed by topical application of 10⁸ pfu AdCMV-PR8.ha and 10⁸ pfu AdCMV-PR8.np 2 weeks later; Group 2, intranasal inoculation of 2.5×10⁷ pfu wild-type adenovirus serotype 5 followed by intramuscular injection of 100 μg pCMV-PR8.ha DNA and 100 μg pCMV-PR8.np DNA 2 weeks later; Group 3, intranasal inoculation of 2.5×10⁷ pfu wild-type adenovirus serotype 5 followed by intranasal inoculation of 2.5×10⁷ pfu AdCMV-PR8.ha and 2.5×107 pfu AdCMV-PR8.np 2 weeks later; Group 4, topical application of 10⁸ pfu AdCMV-PR8.ha and 10⁸ pfu AdCMV-PR8.np; Group 5, topical application of 10⁸ pfu AdCMV-PR8.np; Group 6, topical application of 10⁸ pfu AdCMV-PR8.ha; Group 7, intramuscular injection of 100 μg pCMV-PR8.ha DNA and 100 μg pCMV-PR8.np DNA; Group 8, intranasal inoculation of 2.5×10⁷ pfu AdCMV-PR8.ha and 2.5×10⁷ pfu AdCMV-PR8.np. AdCMV-PR8.ha, an adenovirus vector encoding the A/PR/8/34 hemagglutinin; AdCMV-PR8.np, an adenovirus vector encoding the A/PR/8/34 nuclear protein; pCMV-PR8.ha, a plasmid expression vector encoding the A/PR/8/34 hemagglutinin; pCMV-PR8.np, a plasmid expression vector encoding the A/PR/8/34 nuclear protein. Numbers in parentheses represent the number of animals for each treatment.

Pre-exposure to wild-type adenovirus did not intervene with this mode of vaccination. As shown in the Phase I Final Report, high levels of neutralizing antibody against influenza A/PR/8/34 could be elicited by intranasal inoculation of these vectors even in animals with pre-exposure to adenovirus. Results suggested that protection may be mediated principally by a humoral immune response when animals were immunized by intranasal inoculation of adenovirus recombinants. In contrast to the intranasal route, animals immunized by topical application of AdCMV-PR8.ha and AdCMV-PR8.np were afforded 71% protection from the challenge. However, animals with pre-exposure to adenovirus failed to be protected by NIVS (noninvasive vaccination onto the skin). As shown in the Phase I Final Report, animals immunized by NIVS produced a relatively low level of neutralizing antibody against influenza A/PR/8/34. Like antibodies induced by intranasal vaccines, production of anti-influenza antibodies as provoked by NIVS was not intervened by pre-exposure to adenovirus. Results suggested that protective immunity may be mediated by a cellular immune response when animals were immunized by NIVS, and this immunologic mechanism could be suppressed by pre-existing immunity to the vector. For patients who can take intranasal vaccines without complications due to any respiratory problems, it may thus be appropriate to co-administer adenovirus-based epicutaneous vaccines together with their intranasal counterparts in an attempt to activate both arms of the immune system simultaneously. There is also an urgent need to develop a non-immunogenic vaccine carrier for NIVS in order to vaccinate animals with pre-existing immunity to adenovirus.

Example 16

Elicitation of Anti-HA Antibodies in a Pigtail Macague by NIVS

Figure 14:
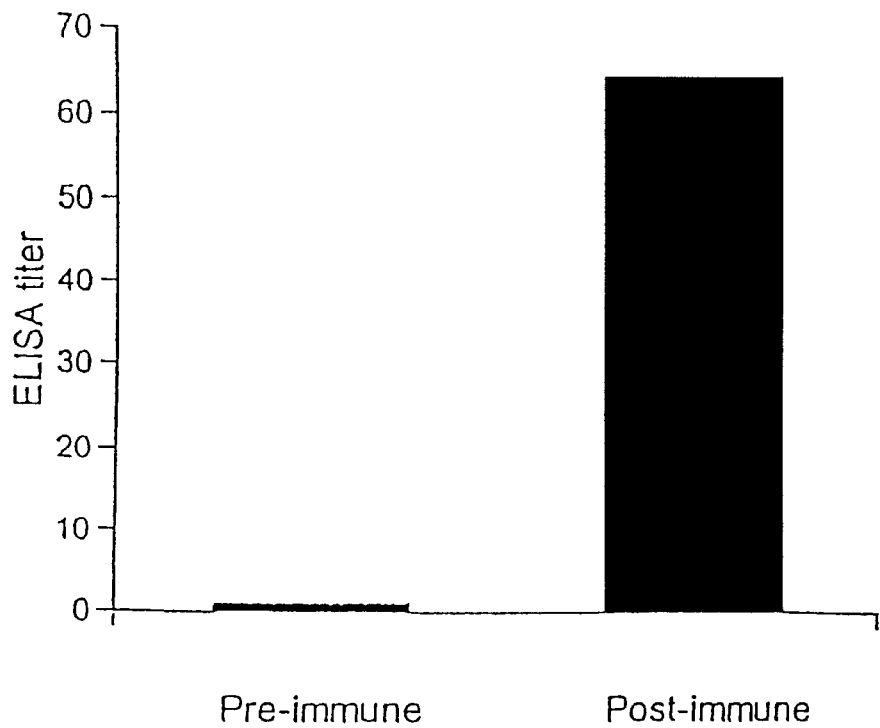
FIG. 14 shows ELISA antibodies generated in a pigtail macaque by a skin patch containing an adenovirus vector encoding influenza HA.

Although NIVS could reproducibly elicit systemic immune responses in mice (FIGS. 12 and 13), it may not be possible for NIVS to immunize humans if transdermal diffusion of vectors should be required for vaccination to occur, because human skin is thicker than its murine counterpart. However, non-invasive vaccine patches may be able to immunize humans or other animals with thick skin if all that is required is a transient but productive wave of antigen expression in cells within the outer layer of skin. To address these issues, we have immunized a pigtail macaque by AdCMV-PR8.ha in a non-invasive mode. As shown in FIG. 14, the immunized animal produced antibodies against HA in 4 weeks. The result provides evidence that non-invasive vaccine patches may be able to inmnunize many different species in addition to mice.

In FIG. 14, a pigtail macaque was immunized in a non-invasive mode by pipetting 10¹⁰ pfu of AdCMV-PR8.ha onto pre-shaved abdominal skin followed by covering the vector as a thin film over naked skin with the Tegaderm patch (3M). Unabsorbed vectors were washed away in 5 hours. Serum samples were assayed for anti-HA antibodies at 4 weeks after inoculation. Titers of anti-HA IgG were determined by ELISA using purified A/PR/8/34 virus as the capture antigen. Serum samples and peroxidase-conjugated goat anti-monkey IgG (Bethyl Laboratories, Inc.) were incubated sequentially on the plates for 1 hour at room temperature with extensive washing between each incubation. The end-point was calculated as the dilution of serum producing the same $OD_{490}$ as a 1/100 dilution of preimmune serum. Sera negative at the lowest dilution tested were assigned endpoint titers of 1.

Example 17

Figure 15:
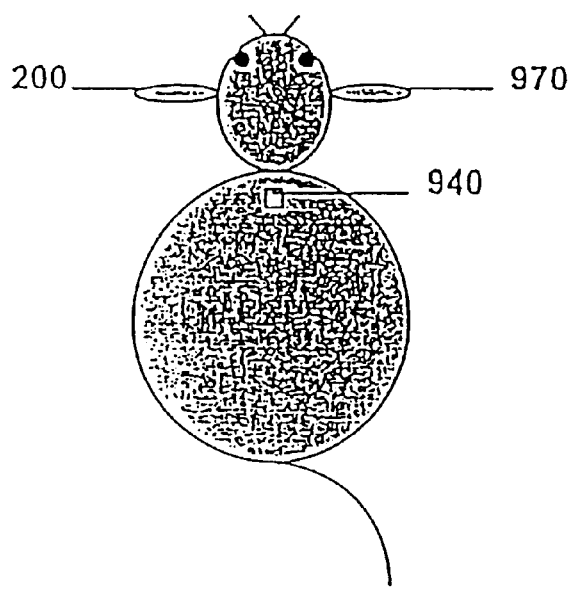
FIG. 15 shows relocation of antigen spots in skin after topical application of an adenovirus vector.

Relocation of Luciferase spots in the Skin after Localized Gene Delivery in a Non-invasive Mode In an attempt to determine whether antigen genes delivered onto the surface of the skin could diffuse into deep tissues and express antigens in cells beyond epidermis, we incubated neck skin with AdCMV-luc (an adenovirus vector encoding luciferase) (Tang et al., 1997). As shown in FIG. 15, luciferase activity could be detected in ears (or as discrete luciferase spots in other areas within the skin) in some of the treated animals one day after non-invasive delivery of AdCMV-luc onto neck skin. Luciferase was undetectable in any of the internal organs including lymph nodes, liver, spleen, heart, lung and kidney.

In FIG. 15, $1\times10^8$ pfu of AdCMV-luc was incubated with neck skin for an hour. Neck skin as well as ears were harvested for luciferase assay as described (Tang et al., 1994) one day after inoculation. Numbers represented light units with background subtracted from the readings.

In a further attempt to identify and characterize the target cells that are able to express the transgene from a topically-applied adenovirus vector, and the putative mobile cells containing the protein expressed from the transgene, we stained skin sections with X-gal after topical application of AdCMV-βgal (an adenovirus vector encoding β-galactosidase) (Tang et al., 1994). By examining histological sections in search of dark blue cells, we identified labeled hair matrix cells within hair follicles and labeled keratinocytes in the outermost layer of epidermis as the principal target cells for adenovirus-mediated transduction when the vector was inoculated in a noninvasive mode (photographs available upon request). None of the dermal fibroblasts were transduced by this procedure, although these cells were highly transducible when AdCMV-βgal was injected intradermally using a needle (photographs available upon request). Results suggested that few, if any, of the adenovirus particles that were topically applied could penetrate into dermis beyond the outer layer of epidermis. Microscopic examination of histologic sections did not reveal any physical abrasions of the transduced skin. Macroscopically, there was no inflammation associated with the treated skin. However, transduced cells could only be visualized within the inoculation area (e.g., neck skin). We were unable to identify dark blue cells in ears or other areas within the skin when luciferase activities could be detected in those areas (FIG. 4), probably because luciferase assay is more sensitive than X-gal-mediated β-galactosidase assay. We hypothesize that some antigen-presenting cells (APCs) may respond to antigens expressed on the surface of the skin by acquiring the antigen. The protein may be degraded rapidly, hence undetectable from internal organs including lymph nodes. The biological significance of this relocation of antigens within the skin is unknown.

Example 18

Amplification of Foreign DNA in Various Tissues after Localized Gene Delivery in a Noninvasive Mode.

Figure 16:
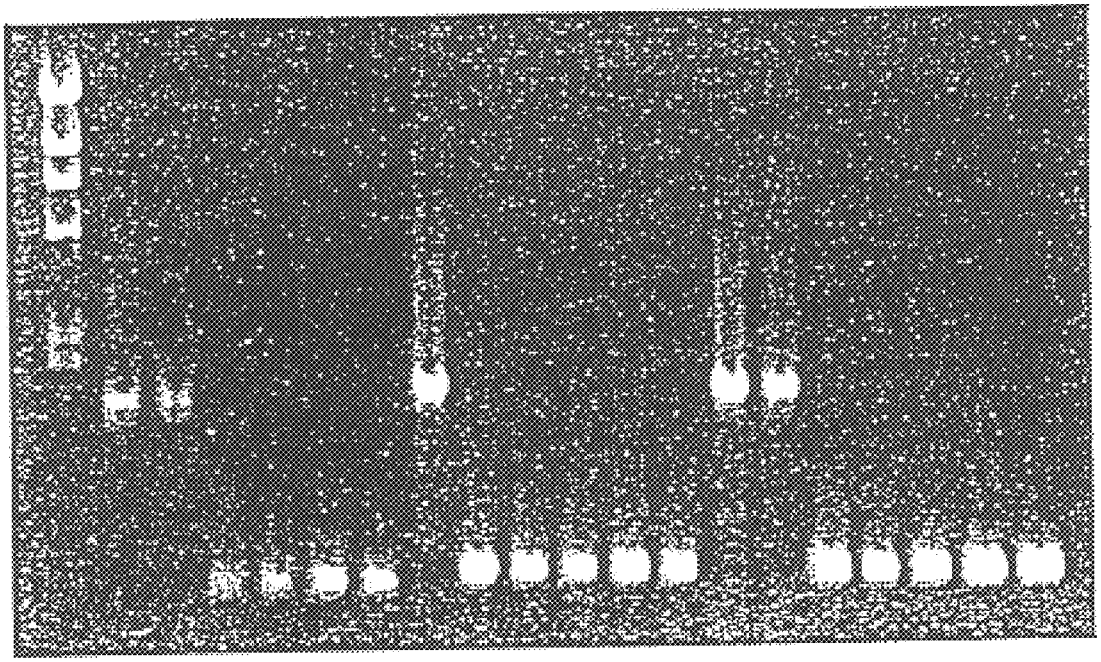
FIG. 16 shows amplification of foreign DNA in various tissues after localized gene delivery in a noninvasive mode.

In an attempt to determine whether topical application of an adenovirus vector can also deliver exogenous DNA beyond the inoculation area, we extracted DNA from various tissues, followed by amplification of the transgene as well as the adenovirus type 5 fiber gene by PCR after noninvasive delivery of AdCMV-PR8.ha onto skin. As shown in FIG. 16, the full-length HA and fiber genes could be amplified from skin 3 hours post-inoculation. The full-length gene was usually undetectable in skin DNA after 1 day or in DNA extracted from other tissues. However, subfragments of both HA and fiber genes could be amplified from liver, whole blood, ear, abdominal skin, or pooled lymph nodes using different sets of primers. No foreign DNA was detectable in any of the tissues 4 weeks post-inoculation. Results suggested that topical application of an adenovirus vector could deliver exogenous DNA into a localized area in skin, although foreign DNA may be rapidly acquired by some putative antigen-presenting cells, degraded, and relocated into deep tissues. The elimination of foreign DNA in 4 weeks highlights the safety of NIVS. In FIG. 16, AdCMV-PR8.ha and AdCMV-luc were inoculated onto pre-shaved skin in a noninvasive mode. DNA was extracted by DNAZOL (GIBCOBRL), and amplified by the following sets of primers:

Ha5.1: 5'-A T G A A G G C A A A C C T A C T G G T-3' (SEQ ID NO:1)

Ha3.1: 5'-G A T G C A T A T T C T G C A C T G C A-3' (SEQ ID NO:2)

Ha5.2: 5'-G T G G G G T A T T C A T C A C C C G T-3' (SEQ ID NO:3)

Ha3.2: 5'-T G C A T A G C C T G A T C C C T G T T-3' (SEQ ID NO:4)

Luc5.1: 5'-G C G C C A T T C T A T C C T C T A G A-3' (SEQ ID NO:5)

Luc3.1: 5'-A C A A T T T G G A C T T T C C G C C C-3' (SEQ ID NO:6)

Luc5.2: 5'-G T A C C A G A G T C C T T T G A T C G-3' (SEQ ID NO:7)

Luc3.2: 5'-C C C T C G G G T G T A A T C A G A A T-3' (SEQ ID NO:8)

Fb5.1: 5'-C C G T C T G A A G A T A C C T T C A A-3' (SEQ ID NO:9)

Fb3.1: 5'-A C C A G T C C C A T G A A A A A T G A C-3' (SEQ ID NO:10)

Fb5.2: 5'-G G C T C C T T T G C A T G T A A C A G-3' (SEQ ID NO:11)

Fb3.2: 5'-C C T A C T G T A A T G G C A C C T G T-3' (SEQ ID NO:12)

Ha5.1 and Ha3.1 amplified the nearly full-length 1.7 kb HA gene; Ha5.2 and Ha3.2 amplified an 0.6 kb subfragment encompassing 33% of the HA gene; Luc5.1 and Luc3.1 amplified the nearly full-length 1.7 kb luciferase gene; Luc5.2 and Luc3.2 amplified an 0.52 kb subfragment encompassing 30% of the luciferase gene; Fb5.1 and Fb3.1 amplified the nearly full-length 1.7 kb adenovirus type 5 fiber gene; Fb5.2 and Fb3.2 amplified an 0.55 kb subfragment encompassing 32% of the fiber gene. Lane M, Molecular weight marker (Lambda DNA cleaved with HindIII); lane 1, the nearly full-length luciferase gene amplified by Luc5.1 and Luc3.1 from skin DNA 3 hours after NIVS; lane 2, the nearly full-length luciferase gene amplified by Luc5.1 and Luc3.1 from skin DNA 1 day after NIVS; lane 3, a subfragment of luciferase DNA amplified by Luc5.2 and Luc3.2 from mouse ear DNA 1 day after NIVS; lane 4, a subfragment of luciferase DNA amplified by Luc5.2 and Luc3.2 from lymph node DNA 1 day after NIVS; lane 5, a subfragment of luciferase DNA amplified by Luc5.2 and Luc3.2 from liver DNA 1 day after NIVS; lane 6, a subfragment of luciferase DNA amplified by Luc5.2 and Luc3.2 from DNA extracted from whole blood 1 day after NIVS; lane 7, the nearly full-length HA gene amplified by Ha5.1 and Ha3.1 from skin DNA 3 hours after NIVS; lane 8, a subfragment of HA gene amplified by Ha5.2 and Ha3.2 from skin DNA 1 day after NIVS; lane 9, a subfragment of HA gene amplified by Ha5.2 and Ha3.2 from lymph node DNA 1 day after NIVS; lane 10, a subfragment of HA gene amplified by Ha5.2 and Ha3.2 from liver DNA 1 day after NIVS; lane 11, a subfragment of HA gene amplified by Ha5.2 and Ha3.2 from kidney DNA 1 day after NIVS; lane 12, a subfragment of HA gene amplified by Ha5.2 and Ha3.2 from DNA extracted from whole blood 1 day after NIVS;

lane 13, the nearly full-length fiber gene amplified by Fb5.1 and Fb3.1 from skin DNA 3 hours after NIVS; lane 14, the nearly full-length fiber gene amplified by Fb5.1 and Fb3.1 from skin DNA 1 day after NIVS; lane 15, a subfragment of fiber gene amplified by Fb5.2 and Fb3.2 from skin DNA 1 day after NIVS; lane 16, a subfragment of fiber gene amplified by Fb5.2 and Fb3.2 from ear DNA 1 day after NIVS; lane 17, a subfragment of fiber gene amplified by Fb5.2 and Fb3.2 from lymph node DNA 1 day after NIVS; lane 18, a subfragment of fiber gene amplified by Fb5.2 and Fb3.2 from liver DNA 1 day after NIVS; lane 19, a subfragment of fiber gene amplified by Fb5.2 and Fb3.2 from DNA extracted from whole blood 1 day after NIVS. DNA from lymph nodes was extracted by pooling inguinal, cervical, and brachial lymph nodes in DNAZOL solution. DNA was amplified for 35 cycles at optimized annealing temperatures in a Stratagene Robocycler gradient 40 thermal cycler. Amplified DNA fragments were fractionated in 1% agarose gel and stained with ethidium bromide.

Example 19

A Depilatory Agent is not Required for NIVS

Figure 17:
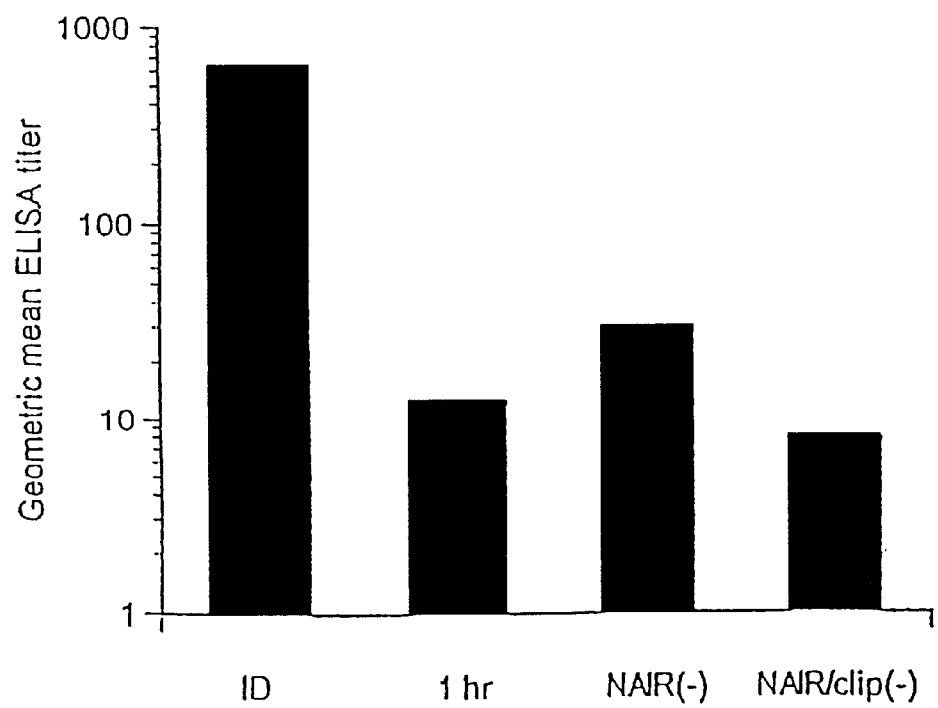
FIG. 17 shows that a depilatory agent such as NAIR is not essential for NIVS.

To determine whether a depilatory agent such as NAIR (Tang et al., 1997) is essential for NIVS, we have compared antibody titers elicited by vaccine patches with or without pre-treatment using NAIR. FIG. 17 shows that antibody titers in mice without NAIR pre-treatment are as high as their counterparts with NAIR pre-treatment. The elimination of NAIR simplifies the NIVS procedure.

In FIG. 17, mice were either injected intradermally (ID) with a dose of $10^8$ pfu, or immunized in a non-invasive mode (NIVS) by pipetting $10^8$ pfu of AdCMV-hcea (Tang et al., 1997) onto abdominal skin followed by covering the vector as a thin film over naked skin with a piece of the Tegaderm patch (3M). Unabsorbed vectors were washed away. Serum samples were assayed for anti-CEA antibodies at 4 weeks after inoculation. Titers of anti-CEA IgG were determined by ELISA using purified human CEA (CalBiochem) as the capture antigen. Serum samples and peroxidase-conjugated goat anti-mouse IgG (Promega) were incubated sequentially on the plates for 1 hour at room temperature with extensive washing between each incubation. The end-point was calculated as the dilution of serum producing the same $OD_{490}$ as a 1/100 dilution of preimmune serum. Sera negative at the lowest dilution tested were assigned endpoint titers of 1. The data was plotted as geometric mean endpoint ELISA titers, where n=4 for ID, n=14 for 1 hr, n=10 for NAIR(-), and n=15 for NAIR/clip(-). ID, intradermal injection; 1 hr, vectors were in contact with the outer layer of skin for an hour with shaving and NAIR pre-treatment; NAIR(-), vectors were in contact with the outer layer of skin overnight with shaving but without NAIR pre-treatment; NAIR/clip (-), vectors were in contact with the outer layer of skin overnight with neither shaving nor NAIR pre-treatment.

Example 20

Figure 18:
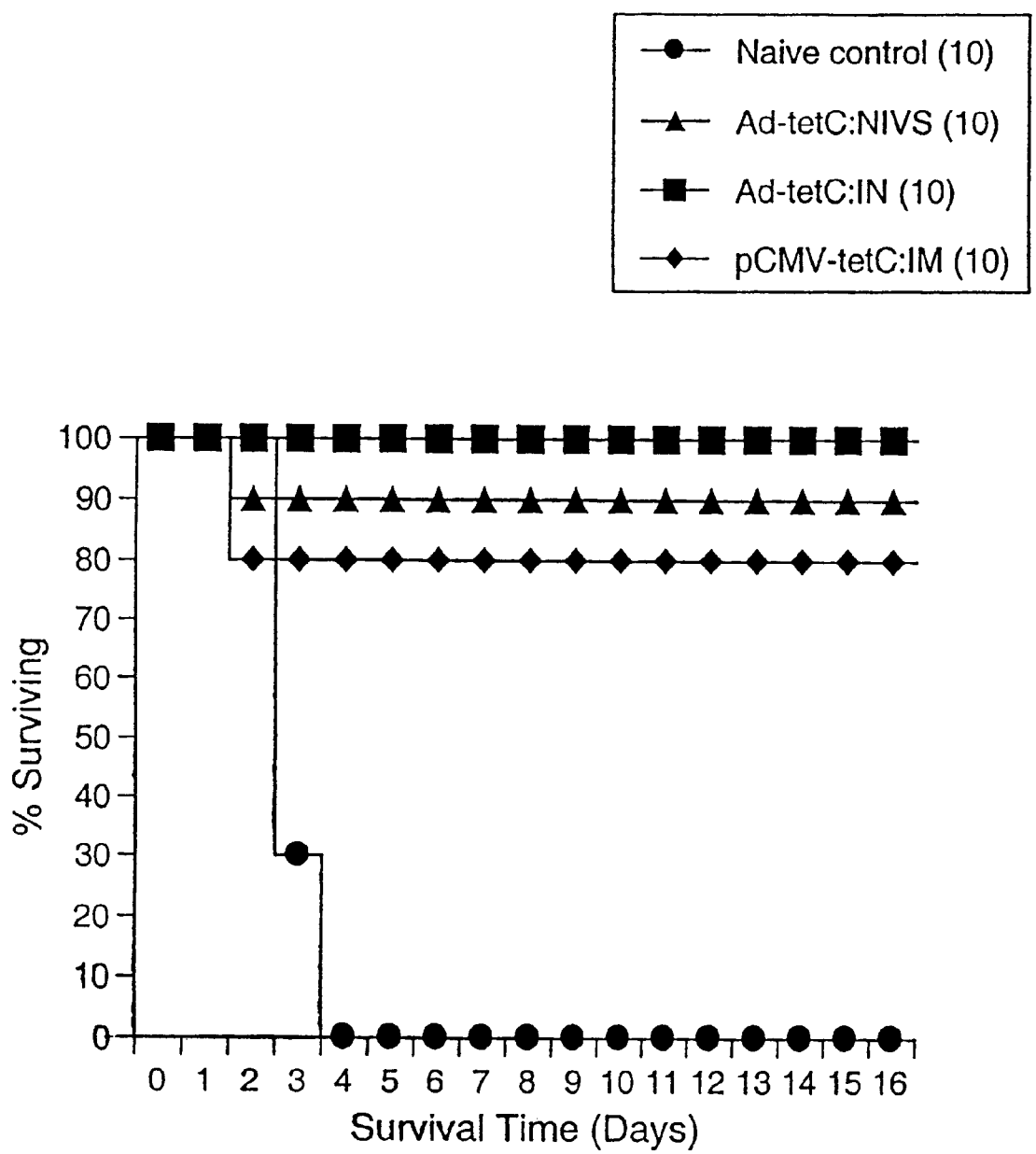
FIG. 18 shows protection from death following *Clostridium tetani* challenge by topical application or intranasal inoculation of an adenovirus-based tetanus vaccine.

As shown in FIG. 18, BALB/c mice (3 months old) were immunized by a variety of vaccination modalities including intramuscular injection of DNA, topical application or intranasal inoculation of an adenovirus-based tetanus vaccine. Skin-targeted noninvasive vaccination was carried out by pipetting approximately $10^8$ pfu AdCMV-tetC onto pre-shaved abdominal skin followed by covering the vector as a thin film over naked skin with a piece of the Tegaderm patch (3M). Unabsorbed vectors were washed away in an hour. Nasal vaccines were administered by pipetting approximately $10^7$ pfa AdCMV-tetC into the nasal cavity. All animals were immunized 3 times every 3 weeks. One week after the last boost, mice were challenged by injecting a lethal dose of *Clostridium tetani* into the footpad and monitored daily for survival. The data was plotted as % survival versus days after challenge. Naïve Control, naïve mice without vaccination prior to challenge. Ad-tetC:NIVS, mice immunized by topical application of AdCMV-tetC; Ad-tetC:IN, mice immunized by intranasal inoculation of AdCMV-tetC; pCMV-tetC:IM, mice immunized by intramuscular injection of 100 g pCMV-tetC DNA. AdCMV-tetC, an adenovirus vector encoding the *Clostridium tetani* toxin C-fragment; pCMV-tetC, a plasmid expression vector encoding the *Clostridium tetani* toxin C-fragment. Numbers in parentheses represent the number of animals for each treatment.

The herein examples involving nasal administration further illustrate that one can achieve a suitable response via mucosal administration; and, that mucous membranes such as those in the oral cavity can be employed as routes for administration, e.g., buccal and perlingual administration are envisioned by the invention and are demonstrated and discussed via herein examples involving nasal administration, as well as by the general teachings herein.

Thus, the invention includes the application of a recombinant vectored vaccine containing one or more genetic inserts that encode an antigen or epitope of interest or an immune stimulus, or a gene-product from a recombinant vaccine, to the buccal surface of the oral cavity, whereby the product(s) encoded by the inserted gene(s) produce an immunological response that may be protective or therapeutic against an infectious disease. The invention further comprehends such recombinant vectored vaccine or geneproduct of a recombinant vaccine incorporated onto, into or adhered to a matrix, forming a carrier mechanism from which the products for immunization may be released onto the buccal surface or into the oral cavity. The invention yet further includes such embodiments wherein the matrix into which the product for immunization is incorporated may be bioactive or inactive and composed of materials which maintain the integrity of the products for immunization; for instance, the matrix material may be composed of polymeric substances such as glucose or other sugars which are biodegradeable, or other biodegradable substances, or materials that are disposable, but may not be biodegradable.

TABLE 1

Detection of transgene expression from genetic vectors delivered by a bandage, the skin was assayed for luciferase

| Incubation time (hours) | LU per cm² skin |
| --- | --- |
| 1 | 0 |
| 1 | 2,100 |
| 2 | 0 |
| 2 | 0 |
| 2 | 6,200 |
| 2 | 7,300 |
| 2 | 13,000 |
| 2 | 48,000 |
| 2 | 1,800 |
| 2 | 13,000 |
| 18 | 830 |
| 18 | 2,400 |
| 18 | 260 |
| 18 | 630 |
| 18 | 1,300,000 |
| 18 | 24,000 |
| 18 | 2,700 |
| 18 | 280 |

TABLE 2

Summary of AdCMV-PR8.ha DNA relocation following topical application

| Time point | Ear pinna | Abdominal skin[a] | Lymph nodes[b] | Spleen | Liver | Kidney | Blood | Muscle[c] |
|---|---|---|---|---|---|---|---|---|
| I. Nearly full-length HA gene | | | | | | | | |
| 3 hr | 0/2 | 2/2 | 0/2 | 0/2 | 0/2 | 0/2 | 0/2 | 0/2 |
| 1 day | 0/3 | 2/3 | 0/3 | 0/3 | 0/3 | 0/3 | 0/3 | 0/3 |
| 1 month | 0/2 | 0/2 | 0/2 | 0/2 | 0/2 | 0/2 | 0/2 | 0/2 |
| II. Subfragment of HA gene | | | | | | | | |
| 3 hr | 0/2 | 2/2 | 0/2 | 0/2 | 0/2 | 0/2 | 0/2 | 0/2 |
| 1 day | 1/3 | 3/3 | 3/3 | 1/3 | 2/3 | 2/3 | 2/3 | 2/3 |
| 1 month | 0/2 | 0/2 | 0/2 | 0/2 | 0/2 | 0/2 | 0/2 | 0/2 |
| III. Nearly full-length fiber gene | | | | | | | | |
| 3 hr | 0/2 | 2/2 | 0/2 | 0/2 | 0/2 | 0/2 | 0/2 | 0/2 |
| 1 day | 1/3 | 3/3 | 0/3 | 0/3 | 0/3 | 0/3 | 0/3 | 0/3 |
| 1 month | 0/2 | 0/2 | 0/2 | 0/2 | 0/2 | 0/2 | 0/2 | 0/2 |
| IV. Subfragment of fiber gene | | | | | | | | |
| 3 hr | 0/2 | 2/2 | 0/2 | 0/2 | 0/2 | 0/2 | 0/2 | 0/2 |
| 1 day | 1/3 | 3/3 | 0/3 | 0/3 | 0/3 | 0/3 | 0/3 | 0/3 |
| 1 month | 0/2 | 0/2 | 0/2 | 0/2 | 0/2 | 0/2 | 0/2 | 0/2 |

[a]Administration site;
[b]pooled lymph nodes;
[c]hind leg quadriceps.

Mice were immunized by topical application of AdCMV-PR8.ha as described in the foregoing Examples and Figures, e.g., description pertaining to FIG. 1. At indicated time points, total DNA was extracted from the tissues and amplified by PCR using specific primer sets as described in the foregoing Examples and Figures, e.g., description pertaining to FIG. 3. The data were presented as the number of animals containing detectable signals for a specific tissue per total number of animals analyzed.

Mice were immunized by intramuscular injection of pCMV-PR8.ha DNA as described in the foregoing Examples and Figures, e.g., description pertaining to FIG. 1. At indicated time points, total DNA was extracted from the tissues and amplified by PCR using specific primer sets as described the foregoing Examples and Figures, e.g., description pertaining to FIG. 3. The data were presented as the number of animals containing detectable signals for a specific tissue per total number of animals analyzed.

TABLE 3

Summary of pCMV-PR8.ha DNA relocation following intramuscular injection

| Time point | Ear pinna | Abdominal skin | Lymph nodes[a] | Spleen | Liver | Kidney | Blood | Muscle[b] |
|---|---|---|---|---|---|---|---|---|
| I. Nearly full-length HA gene | | | | | | | | |
| 3 hr | 2/3 | 0/3 | 3/3 | 1/3 | 0/3 | 0/3 | 1/3 | 3/3 |
| 1 day | 0/3 | 0/3 | 0/3 | 0/3 | 0/3 | 1/3 | 0/3 | 0/3 |
| 1 month | 0/2 | 0/2 | 0/2 | 0/2 | 0/2 | 0/2 | 0/2 | 0/2 |
| II. Subfragment of HA gene | | | | | | | | |
| 3 hr | 3/3 | 1/3 | 3/3 | 2/3 | 3/3 | 2/3 | 3/3 | 3/3 |
| 1 day | 2/3 | 1/3 | 2/3 | 1/3 | 3/3 | 2/3 | 2/3 | 3/3 |
| 1 month | 1/2 | 1/2 | 2/2 | 1/2 | 1/2 | 0/2 | 0/2 | 1/2 |

[a]Pooled lymph nodes;
[b]hind leg quadriceps (administration site).

TABLE 4

Summary of AdCMV-PR8.ha DNA relocation following administration of heat-inactivated adenovirus vectors

| Time point | Ear pinna | Abdominal skin[a] | Lymph nodes[b] | Spleen | Liver | Kidney | Blood | Muscle[c] |
|---|---|---|---|---|---|---|---|---|
| I. Nearly full-length HA gene | | | | | | | | |
| 1 day | 0/3 (3/7) | 1/3 (7/7) | 0/3 (1/7) | 0/3 (0/7) | 0/3 (0/7) | 0/3 (0/7) | 0/3 (0/7) | 0/3 (0/7) |
| II. Subfragment of HA gene | | | | | | | | |
| 1 day | 0/3 (4/7) | 3/3 (7/7) | 0/3 (2/7) | 0/3 (1/7) | 0/3 (1/7) | 0/3 (0/7) | 0/3 (0/7) | 0/3 (0/7) |
| III. Nearly full-length fiber gene | | | | | | | | |
| 1 day | 0/3 (2/7) | 2/3 (6/7) | 0/3 (1/7) | 0/3 (0/7) | 0/3 (1/7) | 0/3 (0/7) | 0/3 (0/7) | 0/3 (0/7) |
| IV. Subfragment of fiber gene | | | | | | | | |
| 1 day | 0/3 (2/7) | 3/3 (7/7) | 0/3 (2/7) | 0/3 (0/7) | 0/3 (2/7) | 0/3 (1/7) | 0/3 (1/7) | 0/3 (0/7) |

[a]Administration site;
[b]pooled lymph nodes;
[c]hind leg quadriceps.

Summary of AdCMV-PR8.ha DNA relocation following topical application:

AdCMV-PR8.ha particles were inactivated by heating at 95° C. for 10 min. Vectors were administered to mice either by topical application as described in the foregoing Examples and Figures, e.g., description pertaining to FIG. 1, or by intradermal injection of an equivalent amount of vectors using a needle. One day following localized gene delivery, total DNA was extracted from various tissues. Nearly full-length HA and fiber genes and their subfragment counterparts were amplified by PCR using specific primer sets as described in FIG. 3 legend. The data were presented as the number of animals containing detectable signals for a specific tissue per total number of animals analyzed. Numbers without parentheses represent topical application; numbers in parentheses represent intradermal injection. Significance: It is possible that vector DNA may relocate to distant tissues following topical application by three different mechanisms: (1) translocation across skin by diffusion followed by relocation via circulation, (2) translocation across skin followed by subsequent pinocytotic uptake into antigen-presenting cells (APCs), (3) transduction of keratinocytes followed by intercellular transfer of exogenous biomolecules into APCs. Although heat-inactivated adenovirus vectors are incapable of transducing cells as shown by their failure to produce cytopathic effects (CPE) in human 293 cells probably due to denaturation of essential ligands (e.g., CAR and RGD motif), they should still be able to diffuse into the skin as live vectors do if diffusion should occur. Results show that the principal mechanism mediating vector DNA relocation following NIVS was unlikely due to translocation across skin by diffusion. Topical application of adenovirus vectors may thus represent a noninvasive rather than a transdermal vaccination modality.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

Barry, M. A. et al. Protection against mycoplasma infection using expression-library immunization. *Nature* 377, 632–635 (1995).

Conry, R. M. et al. A carcinoembryonic antigen polynucleotide vaccine for human clinical use. *Cancer Gene Ther.* 2, 33–38 (1995).

Cotten, M. et al. High-efficiency receptor-mediated delivery of small and large (48 kilobase) gene constructs using the endosome-disruption activity of defective or chemically inactivated adenovirus particles. *Proc. Natl. Acad. Sci USA* 89, 6094–6098 (1992).

Glenn, G. M. et al. Skin immunization made possible by cholera toxin. *Nature* 391, 851 (1998).

Gomez-Foix et al. Adenovirus-mediated transfer of the muscle glycogen phosphorylase gene into hepatocytes confers altered regulation of glycogen metabolism. *J. Biol Chem.*, 267, 25129–25134 (1992).

Johnston, S. A. & Tang, D.-c. Gene gun transfection of animal cells and genetic immunization. *Meth. Cell Biol.* 43, 353–365 (1994).

McDonnell, W. M. & Askari, F. K. DNA vaccines. *New Engl. J Med.* 334, 42–45 (1996).

Tang, D.-c. et al. Genetic immunization is a simple method for eliciting an immune response. *Nature* 356, 152–154(1992).

Tang, D.-c. et al. Butyrate-inducible and tumor-restricted gene expression by adenovirus vectors. *Cancer Gene Ther.* 1, 15–20 (1994).

Tang, D.-c. et al. In vivo cytotoxicity assay for assessing immnunity. *J. Immunol. Methods* 189, 173–182 (1996).

Tang, D.-c. et al. Vaccination onto bare skin. *Nature* 388, 729–730 (1997).

What is claimed is:

1. A method of non-invasively inducing a systemic immune response, comprising topically administering, an adenoviral vector that encodes a gene of interest and expresses a protein encoded by the gene of interest, to the skin of a mammal, in an effective amount to induce said systemic immune response to said protein, wherein a systemic immune response to said protein is induced in said mammal.

2. The method of claim 1, wherein the protein comprises an antigen or an immunogenic fragment thereof.

3. The method of claim 2, wherein the antigen or immunogenic fragment thereof is expressed to produce a systemic immune response against a pathogen or neoplasm.

4. The method of claim 2, wherein the antigen is selected from the group consisting of the human carcinoembryonic antigen, the HIV gp120 antigen, the tetanus toxin C-fragment, the influenza NP antigen, and the influenza HA antigen.

5. The method of claim 2, wherein the antigen comprises a tumor associated antigen.

6. The method of claim 1, wherein the amount of the adenoviral vector is at least approximately 100 plaque forming units.

7. The method of claim 1, wherein the adenoviral vector further comprises and expresses an immune modulatory gene.

8. The method of claim 7, wherein the immune modulatory gene is selected from the group consisting of a GM-CSF gene, a B7-1 gene, a B7-2 gene, an interleukin-2 gene, an interleukin-12 gene and an interferon gene.

9. The method of claim 1, wherein the adenoviral vector further comprises and expresses a co-stimulatory gene and a cytokine gene.

10. The method of claim 1, wherein the adenoviral vector is defective in its E1 region.

11. The method of claim 1, wherein the adenoviral vector is defective in its E4 region.

12. The method of claim 1, wherein the adenoviral vector is defective in its E3 region.

13. The method of claim 1, wherein the adenoviral vector has all viral genes deleted.

14. The method of claim 1, wherein the adenoviral vector is defective in E1 and E3 regions.

15. The method of claim 1, wherein the adenoviral vector is defective in E1, E3 and E4 regions.

16. The method claim 1, wherein the systemic immune response is a protective systemic immune response.

17. The method of claim 1, further comprising disposing the adenoviral vector on a delivery device and the step of topically administering the adenoviral vector comprises topically applying the device to the skin of the mammal.

18. The method of claim 17, wherein the device includes a pad.

19. The method of claim 17, wherein the device includes an adhesive-bandage-like device.

20. The method of claim 17 wherein, said device comprises:

a skin contacting means comprised of a first sheet of material having a first side and a second side, said first side adapted to contact the surface of the skin of the mammal, and a second sheet of material having a first side disposed opposite to said first side of said first sheet;

said first sheet and said second sheet are bonded together around external portions thereof to define a central enclosed space therebetween for containing the adenoviral vector therein; and said material comprising said first sheet being structurally weaker than said material comprising said second sheet whereby when the adenoviral vector is disposed in said space, and when a force is applied to said first side of said second sheet, said first sheet breaks before said second sheet allowing the adenoviral vector to contact the skin of the mammal.

21. The method of claim 20 wherein in the device, said first side of said first sheet includes an adhesive disposed about the periphery thereof to affix said device to the surface of the skin of the mammal wherein the portion of said first sheet superimposed over said space is substantially free of adhesive.

22. The method of claim 20 wherein in the device, said sheets are comprised of a material impermeable to the adenoviral vector.

23. The method of claim 20 wherein in the device, said sheets are comprised of polymeric material.

24. The method of claim 1, wherein said mammal is shaved at the site of the topical administration.

25. A method of non-invasively inducing a systemic immune response comprising topically administering a DNA viral vector complex that encodes a gene of interest and expresses a protein encoded by the gene of interest, to the skin of a mammal, in an effective amount to induce said systemic immune response to said protein, wherein a systemic immune response to said protein is induced in said mammal.

26. The method of claim 25, wherein the DNA is in plasmid form.

27. The method of claim 26, wherein the virus is an adenovirus.

28. The method of claim 26, wherein said mammal is shaved at the site of the topical administration.

29. The method of claim 25, wherein the virus is an adenovirus.

30. The method according to claim 25, wherein said viral vector complex is constructed comprising the steps of:

providing a suitable DNA viral vector;

providing a DNA sample which encodes the gene of interest to be complexed with the viral vector; and mixing together the viral vector and the DNA sample in the presence of a polycation.

31. The method of claim 30, wherein said viral vector is an adenovirus.

32. The method of claim 31, wherein the polycation comprises poly-L-lysine and the ratio of the poly-L-lysine (PLL) to adenovirus vector ranges from between 6.0 $\mu$g PLL: $10^8$ plaque forming units adenovirus to 6.0 $\mu$g PLL: $10^{10}$ plaque forming units adenovirus.

33. The method of claim 30, wherein the gene of interest encodes an antigen or immunogenic fragment thereof.

34. The method of claim 30, wherein the polycation comprises poly-L-lysine and the ratio of the poly-L-lysine (PLL) to DNA sample ranges from between approximately 0.9 $\mu$g PLL:1.0 $\mu$g DNA to 9.0 $\mu$g PLL: 1 $\mu$g DNA.

35. The method of claim 25, wherein said mammal is shaved at the site of the topical administration.

36. A method of non-invasively inducing a systemic immune response, comprising topically administering, a DNA viral vector that encodes a gene of interest and expresses a protein encoded by the gene of interest, to the skin of a mammal, in an effective amount to induce said systemic immune response to said protein, wherein a systemic immune response to said protein is induced in said mammal.

37. The method of claim 36, wherein the protein comprises an antigen or immunogenic fragment thereof.

38. The method of claim 37, wherein the antigen or immunogenic fragment thereof is expressed to produce a systemic immune response against a pathogen or neoplasm.

39. The method of claim 37, wherein the antigen comprises a tumor-associated antigen.

40. The method of claim 37, wherein the antigen is selected from the group consisting of the human carcinoembryonic antigen, the HIV gp120 antigen, the tetanus toxin C-fragment, the influenza NP antigen, and the influenza HA antigen.

41. The method of claim 36, wherein the vector further comprises and expresses an immune modulatory gene.

42. The method of claim 36, wherein the vector further comprises and expresses a co-stimulatory gene and a cytokine gene.

43. The method of claim 42, wherein the immune modulatory gene is selected from the group consisting of a GM-CSF gene, a B7-1 gene, a B7-2 gene, an interleukin-2 gene, an interleukin-12 gene and an interferon gene.

44. The method of claim 36, wherein said mammal is shaved at the site of the topical administration.

45. The method of claim 36 further comprising disposing the vector on a delivery device and the step of topically administering the vector comprises topically applying the device to the skin of the mammal.

46. The method of claim 45, wherein the device includes a pad.

47. The method of claim 45, wherein the device includes an adhesive bandage-like device.

48. The method of claim 45 wherein, said device comprises:

a skin contacting means comprised of a first sheet of material having a first side and a second side, said first side adapted to contact the surface of the skin of the mammal, and a second sheet of material having a first side disposed opposite to said first side of said first sheet;

said first sheet and said second sheet are bonded together around external portions thereof to define a central enclosed space therebetween for containing the vector therein; and said material comprising said first sheet being structurally weaker than said material comprising said second sheet whereby when the vector is disposed in said space, and when a force is applied to said first side of said second sheet, said first sheet breaks before said second sheet allowing the vector to contact the skin of the mammal.

49. The method of claim 48 wherein in the device, said first side of said first sheet includes an adhesive disposed about the periphery thereof to affix said device to the surface of the skin of the mammal wherein the portion of said first sheet superimposed over said space is substantially free of adhesive.

50. The method of claim 48 wherein in the device, said sheets are comprised of a material impermeable to the vector.

51. The method of claim 48 wherein in the device, said sheets are comprised of polymeric material.

52. A method of non-invasively inducing a protective systemic immune response, comprising topically administering, a DNA viral vector that encodes a gene of interest and expresses a protein encoded by the gene of interest, to the skin of a mammal, in an effective amount to induce said protective systemic immune response to said protein, wherein a systemic immune response to said protein is induced in said mammal; and, wherein said protein comprises an antigen or immunogenic fragment thereof.

* * * * *